United States Patent [19]

Hansen, Jr. et al.

[11] Patent Number: 4,727,189
[45] Date of Patent: Feb. 23, 1988

[54] SUBSTITUTED TYROSYL ALANINE DIPEPTIDE AMIDES

[75] Inventors: Donald W. Hansen, Jr.; Robert H. Mazur, both of Chicago; Daniel R. Pilipauskas, Glenview, all of Ill.

[73] Assignee: G. D. Searle & Co., Chicago, Ill.

[21] Appl. No.: 851,834

[22] Filed: Apr. 14, 1986

Related U.S. Application Data

[63] Continuation of Ser. No. 692,611, Jan. 22, 1985, Pat. No. 4,599,325, which is a continuation-in-part of Ser. No. 580,977, Feb. 16, 1985, abandoned.

[51] Int. Cl.$^4$ .................... C07C 103/20; C07C 68/00
[52] U.S. Cl. ..................................... 564/155; 558/273
[58] Field of Search .................. 514/19; 564/155; 558/273

[56] References Cited

U.S. PATENT DOCUMENTS 4,599,325  7/1986  Hansen, Jr. et al. ............... 514/19

Primary Examiner—Delbert R. Phillips
Attorney, Agent, or Firm—Frank P. Grassler; J. Timothy Keane; Paul D. Matukaitis

[57] ABSTRACT

The invention relates to novel substituted tyrosyl alanine dipeptide amides of the formula:

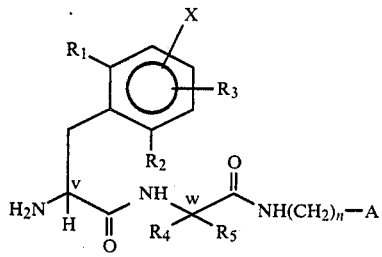

and the pharmaceutically acceptable acid addition salts thereof wherein $R_1$ represents straight or branched lower alkyl having 1 to 4 carbons;

$R_2$ represents hydrogen, hydroxy, $-OCO_2R_1$ substituent or lower alkyl having 1 to 4 carbons;

$R_3$ represents a hydrogen or lower alkyl having 1 to 6 carbons;

$R_4$ and $R_5$ may be the same or different and represent hydrogen or lower alkyl having 1 to 6 carbons;

n is 1 to 6;

X represents a hydrogen, hydroxy or $OCO_2R_1$ substituent;

A represents a cyclohexyl, phenyl or phenyl substituted with one or more lower alkyls containing 1 to 6 carbons, one or more amino, hydroxy, halogen, nitro or lower alkoxy substituent having 1 to 6 carbons;

V represents the asymmetric carbon that may be racemic or have the D or L configuration;

W represents the asymmetric carbon when $R_4$ and $R_5$ are not the same that may optionally be racemic or have the D or L configuration.

These compounds are useful as analgesic and/or antihypertensive agents.

4 Claims, No Drawings

SUBSTITUTED TYROSYL ALANINE DIPEPTIDE AMIDES

This is a continuation of application Ser. No. 06/692,611, filed Jan. 22, 1985, now U.S. Pat. No. 4,599,325, which is a continuation-in-part of application Ser. No. 06/580,977, filed Feb. 16, 1985, now abandoned.

FIELD OF THE INVENTION

The present invention relates to novel dipeptide amides. In particular, it provides novel dipeptide derivatives of Formula 1 which are useful as analgesic or antihypertensive agents.

BACKGROUND OF THE INVENTION

In 1975, a pentapeptide, methionine enkephalin, was reported by Hughes et al., *Nature*, 258, 577 (1975). This peptide is found in many areas of the brain where it appears to act as a neurotransmitter or neuromodulator in a central pain-suppressant system. The natural peptide binds stereospecifically to partially purified brain opiate receptor sites, see for example, Bradberry et al., *Nature*, 260, 793 (1976). The natural peptide is also highly active in bioassays for opiate activity but exhibits only weak, fleeting analgesic activity when injected directly into the brain of the rat, see for example, Belluzi et al., *Nature*, 260, 625 (1976)

In order to overcome the lack of in vivo activity, a number of investigators have made numerous modifications in the methionine enkephalin structure, such as substituting the glycine in the 2-position with a D-amino acid, N-methylation of the L-tyrosine, substituting the 4-phenylalanine with, for example, methyl or halo, modifying the C-terminus, etc., to produce enkephalin derivatives of varying properties and potencies.

Kiso, et al., "Peptide Chemistry 1981,": 65–70, Protein Research Foundation, Osaka, Japan (1982), disclosed the synthesis and activity of short chain enkephalin-like peptides, among them tripeptide and dipeptide alkylamides such as N-methyl tyrosine (D) methionine sulfoxide glycine-methylphenethylamide (2) and tyrosine-(D) methionine sulfoxide phenylpropyl amide (3).

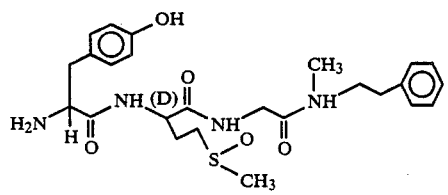

(2)

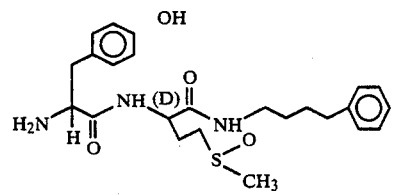

(3)

Vavrek, et al., Peptides 2, 303, 1981 disclosed analogs of enkephalin, among them the dipeptide tyrosine-D-alanine-phenylpropylamide (Tyr-(D) Ala-PPA) (4).

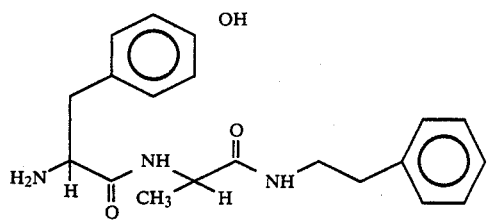

(4)

A comparison of the Vavrek, et al. compound and a compound of the present invention is illustrated in Table 2 of Example 78. The compound of this invention has unexpected and surprisingly superior properties when compared to the Vavrek compound. The present invention provides new mini enkephalin derivatives which show improved potency as analgesic agents by both oral and parenteral routes of administration.

U.S. Pat. No. 4,316,892 relates to certain derivatives of methionine enkephalin derivatives useful as analgesic agents.

SUMMARY OF THE INVENTION

A compound of the formula:

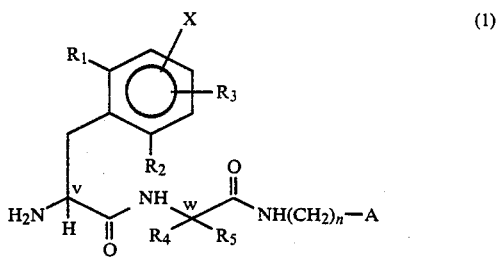

(1)

and the pharmaceutically acceptable acid addition salts thereof wherein $R_1$ represents lower alkyl having 1 to 4 carbons;

$R_2$ represents hydrogen, hydroxy, $OCO_2R_1$ substituent or lower alkyl having 1 to 4 carbons;

$R_3$ represents a hydrogen or lower alkyl having 1 to 6 carbons;

$R_4$ and $R_5$ may be the same or different and represent hydrogen or lower alkyl having 1 to 6 carbons;

n is 1 to 6;

X represents a hydrogen, hydroxy or $OCO_2R_1$ substituent;

A represents a cyclohexyl, phenyl or phenyl substituted with one or more lower alkyl containing 1 to 6 carbons, one or more amino, hydroxy, halogen, nitro or lower branched alkoxy substituent having 1 to 6 carbons;

V represents the asymmetric carbon that may optionally be racemic or have the D or L configuration;

W represents the asymmetric carbon when $R_4$ and $R_5$ are not the same that may optionally be racemic or have the D or L configuration.

Preferred embodiments are compounds of the formula:

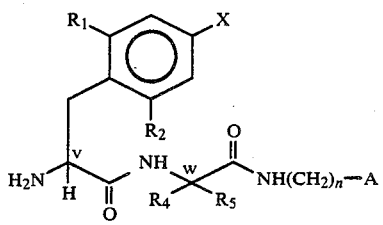

and the pharmaceutically acceptable salts thereof where the variable are as earlier defined.

More preferred embodiments are compounds of the formula:

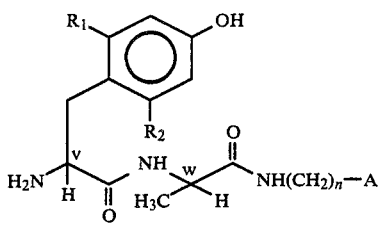

and the pharmaceutically acceptable salts thereof where the variables are as previously defined. The embodiment where n is 3 and A is phenyl or cyclohexyl are especially preferred. Further preferred embodiments appear in the examples.

BRIEF DESCRIPTION OF THE FLOW-SHEETS

Flow-sheet 1 illustrates Route A for the synthesis of substituted tyrosyl alanine dipeptide amides wherein the alanine-amide mixed anhydride coupling occurs first followed by its mixed anhydride coupling with the substituted tyrosine. The substituents are as defined in summary of the invention.

Flow sheet 2 illustrates Route B for the synthesis of substituted tyrosyl alanine dipeptide amides wherein the substituted tyrosine-alanine mixed anhydride coupling occurs first followed by its mixed anhydride coupling with the amide. The substituents are as defined in summary of the invention.

DESCRIPTION OF THE SPECIFIC EMBODIMENTS

The compounds described in this invention and illustrated in Examples 1–77 are synthesized by either of two procedures illustrated in flow sheet 1 and 2 as Route A and Route B. Many of the compounds can be prepared by either route with the principal difference being the reaction sequence.

ROUTE A

In Route A the blocked (D)Ala is coupled with the amino-alkyl-A (Compound I) by a mixed anhydride reaction. A is defined as a cyclohexyl or phenyl optionally substituted with one or more lower alkyl groups having 1 to 6 carbons, one or more amino, hydroxyl, halogen (F, Cl, Br, or I), nitro, or lower alkoxy having 1 to 6 carbons. In all cases the use of the term "lower alkyl or alkoxy" includes both straight and branched chains. Alkylene radicals formed by n=2 to 6 are also straight or branched chain. The mixed anhydride reaction coupling compound I and Z-(D)Ala-OH results in compound II. Z represents carbobenzoxy or other similar blocking groups.

Compound II is deblocked using hydrogen/Pd in ethanol resulting in compound IV. A blocked and optionally substituted (D, L or DL) tyrosine (Compound III) is coupled with Compound IV by a mixed anhydride reaction to produce Compound V which is a mixture of separable diaesteomers when a racemic Compound III is used.

The substituted tyrosine (Compound III) contains $R_1$ representing hydrogen, lower alkyl having 1 to 4 carbons such as methyl, ethyl, n-propyl isopropyl, n-butyl isobutyl or sec-butyl; $R_2$ representing lower alkyl having 1 to 4 carbons as defined above, hydroxy, $OCO_2R_1$ such as methyl, ethyl, propyl, isopropyl, n-butyl, sec-butyl or isobutyl carbonate; $R_3$ is representing hydrogen, straight or branched lower $C_1$ to $C_6$ alkyl as defined in $R_1$ plus n-pentyl, iso-pentyl, sec-pentyl, neopentyl, n-hexyl, iso-hexyl, sec-hexyl and the like; X representing an optional hydroxy or $-OCO_2R_1$ on carbon 3, 4 or 5 of the aromatic ring; and the chirol carbon "v" is D, L, or DL. When v is DL, the Compound V is generated as a mixture of separable diastereomeric Compounds VI and VII. The separation is carried out by crystalization or chromotography as described in Example 3. Each diastereomer is deblocked with HCl to give Compounds VIII and IX as demonstrated in Examples 4 and 5.

ROUTE B

In Route B the blocked amino acid (Compound III) is coupled by a mixed anhydride reaction with (D) Ala methyl ester to give the dipeptide (Compound X) as described in Example 6. Where V is DL, two separable diastercomers are represented by Compound X. Fractional crystallization is used to separate diaestereomers XI and XII as described in Examples 6. Each isomer is saponified to produce the free acids. Each of these free acids is independently coupled by a mixed anhydride reaction with Compound I to produce diastereomers VI and VII as described in Examples 13 and 14. Each of these compounds is deblocked with HCl to produce the final products XIII and IX.

Modified Alanine Route

Additional compounds as of this invention are synthesized using the procedures of Route A or Route B with the alanine replaced by $NHCR_4R_5CO$(D, L, or DL). Both $R_4$ and $R_5$ represent hydrogen or straight or branched lower alkyl having 1 to 6 carbons as described previously for $R_3$. Following the procedures for Route A and B, as illustrated in examples 1 through 43, one produces compounds where the alanine has been modified to lose the asymmetric carbon due to the presence of 2 hydrogen, methyl, ethyl, propyl, butyl, pentyl or hexyl substituents. If non-identical $R_4$ and $R_5$ groups are present the asymmetric carbon is preserved and may be D, L or DL. Among the alanine replacements produced in this series are other common D and L amino acids such as glycine, leucine, isoleucine, and valine.

In the modified Route A and Route B incorporating $NHCR_4R_5CO$, if desired, the production of racemic mixtures can be avoided by starting with enanteomerically pure forms of the compounds. The use of these compounds is obvious to those skilled in the art. Failure to use these enanteomerically pure forms results in isomeric mixtures that may be difficult to separate.

The analgesic activity for the compounds of the present invention is illustrated by their activity in the following tests: the tail flick test, the hot plate test and the writhing test. The analgesic activity of the representative compounds was compared with that of a disclosed analog of enkephalin, tyrosine-(D)-alaninephenylpropylamide.

Combined Tail Flick and Hot Plate Tests

(subcutaneous and oral administration)

Male albino inbred mice supplied by Charles River (CD-1/HAM/1LR) weighing between 20 and 30 grams were used. Analgesia was first measured using the tail flick test in which a high intensity beam of light was focused on the blackened tail. The interval of time between onset of the light and reflex removal of the tail was defined as the tail flick latency. The average of two successive determinations was recorded. Following tail flick determination, the animals were immediately placed on a 55° C. copper hot plate to which they were restricted by an inverted 600 ml glass beaker. Hot plate latency was defined as the interval between placement on the hot plate and a behavioral response of either a jump or a hindpaw lick. One determination was recorded. Mice not responding within 4.0 seconds on the tail flick and 20.0 seconds on the hot plate were discarded from the study. The tail flick test and the hot plate test were stopped after 12.0 and 40 seconds, respectively, had elapsed to prevent tissue damage. After determination of pre-injection baseline latencies, the test compound was dissolved in distilled water and administered either orally or subcutaneously (0.1 ml/10 gram body weight). Tail flick and hot plate latencies were measured 10, 30, 60 and 90 minutes after injection. One-way analyses of variance were used to detect any significant increase in tail flick and hot plate latencies (indicative of analgesia) as compared to latencies prior to drug administration, as well as to establish the dose-dependence of any effect. A linear regression method (least squares) was used to determine the line of best fit. The $ED_{50}$ dose was determined to be that dose of test compound that produced one-half the maximum measurable increase in latency. This corresponded to a post-drug tail flick latency of 7.5 seconds and hot plate latency of 25 seconds. G. Keppel: *Design and analysis: a reasearcher's handbook*, New Jersey, Prentice-Hall, 1973.

Writhing assay

Male Charles River albino mice (CD-1/HAM/1LR) weighing between 20 and 30 grams were used. Thirty minutes after subcutaneous or intragastric administration of the test compound (0.1 ml/10 gram body weight), 0.025% (w/v) phenylbenzoquninone was injected intraperitoneally (0.1 ml/10 gram body weight). Five minutes later, each mouse was placed in a large glass beaker and the number of writhes that occurred in the subsequent ten minutes is counted. A writhe consisted of dorsoflexion of the back, extension of the hindlimbs, and strong contraction of the abdominal musculature. The test compound was considered to have produced analgesia in a mouse if the number of writhes elicited by phenylbenzoquinone was equal to or less than one-half the median number of writhes recorded for the saline-treated group that day. The results were expressed as the number of mice (out of a possible ten) in which the test compound produced analgesia. The test compound was rated active if writhing was inhibited (as described) in 5 or 10 mice. If the initial test dose of 10 mg/kg inhibited writhing in greater than 6 of 10 mice, the effect of additional doses was evaluated and an $ED_{50}$ value was calculated using a maximum likelihood function.

Hot Plate Test (intravenous administration)

Male albino inbred mice supplied by Charles River [CD-1 (ICR)BR] weighing between 20 and 30 grams were used. The mice were placed on a 55° C. hot plate 60, 40, and 20 minutes prior to drug administration and the latencies to the lick of a paw or to a jump were recorded. Mice not responding within 15 seconds were discarded from the study. The test compound or vehicle was then administered intravenously and the animals' response latencies on the hot plate were recorded again 10, 30 and 60 minutes later. The initial test dose was 10 mg/kg. Mice not responding within 30 seconds were removed from the hot plate to prevent tissue damage and assigned the cut-off value of 30 seconds. Elevation of the response latencies to greater than twice the median of the three pre-drug latency measurements was indicative of analgesia. For each time point, the data were expressed as the number of animals having analgesic response latencies out of the total number tested. The number of analgesic animals in the test compound-treated group was then compared with the number of analgesic animals in the vehicle-treated group at each time point using Fisher's Exact Probability Test. S. Siegel, *Nonparametric Statistics for the Behavioral Sciences*. McGraw-Hill, New York, pp. 96–104 (1956). A dose of the test compound was considered to be active if the number of animals having analgesic response latencies in the test compound-treated group was significantly greater than the number in the vehicle-treated group.

Cholera-induced Intestinal Fluid Secretion

The rat cholera model was used to determine the effect of the test compounds on intestinal fluid movements. (H. I. Jacoby and C. H. Marshall, Antagonism of Cholera Enterotoxin by Anti-inflammatory Agents in the Rat. *Nature*, 235, 163–165, 1972). Female Charles River rats weighing 85–100 grams and having free access to water were fasted for 24 hours prior to each experiment. After a midline incision was made under ether anesthesia, a 20-cm ligated small intestinal segment was constructed starting 3 cm distal to the ligament of Treitz. Each segment was injected, using a 27 gauge ½-inch needle, with crude cholera toxin in a 0.9% saline solution. Thirty minutes before cholera toxin was injected, test compounds were administered subcutaneously to groups of four rats at doses of 10 and 20 mg/kg. Four hours after injection of toxin, the animals were sacrificed and the fluid content and exact length of the intestinal segments were measured. Fluid secretion was expressed in ml/cm of intestine.

The $ID_{50}$'s of these compounds were estimated using data obtained from at least two doses and at least two experiments by the method of maximum likelihood. R. A. Fischer. "Principles of Statistical Estimation." in *Statistical Methods for Research Workers*, 14th ed. Hafner: New York; pp. 301–339. Lower and upper limit values for the $ID_{50}$, between which the likelihood was more than one-twentieth of its maximum, were used to define an interval of estimation, approximating a 95% confidence interval. The routine calculation did not include a test of the slope of the dose-response curve.

Opiate Binding Assay

The test compounds were evaluated for their ability to displace the binding of $^3$H-Naloxone to opiate receptors isolated from rat brain. Male rats [COBS CD(SD)BR] obtained from Charles River Laboratories (Portage, MI) were sacrificed by cervical dislocation. A purified homogenate of receptor membranes was prepared from the brains according to the method described by Chang and Cuatrecasas. (K.-J. Chang and P. Cuatrecases. Multiple Opiate Receptors: Enkephalins And Morphine Bind To Receptors Of Different Specificity. *J. Biol. Chem.* 254, 2610–2618 (1979).) The brains were homogenized in 10 volumes of 0.32M sucrose and centrifuged twice at 6,000xg for 15 minutes. Following centrifugation of the supernatants at 40,000xg for 30 minutes, the pellets were allowed to swell, then centrifuged at 6,000 and 40,000xg. This process was repeated. The final pellet was resuspended in 2 volumes of 50 mM tris HCl (pH 7.4). The homogenate was assayed for protein content according to the method of Itzhaki and Gill. R. F. Itzhaki and D. M. Gill. A Micro-Biuret Method for Estimating Proteins. *Anal. Biochem.* 9, 401–401 (1964).

The binding of the test compounds to the receptor membrane preparation was measured using a modification of the method of Pert and Snyder. C. G. Pert and S. H. Snyder. Properties of Opiate-Receptor Binding in Rat Brain. *Proc. Natl. Acad. Sci.* 70, 2243–2247 (1973). The receptor assay was run using 1 nM $^3$H-Naloxone and 2 ml of tissue homogenate (0.5 mg/ml protein concentration). Levorphanol ($1 \times 10^{-5}$M) was used as the displacer for non-specific binding. Both the displacer and the test compounds were added in 0.02 ml volumes. The assay was run in 0.05M tris HCl (pH 7.4)±100 mM NaCl. Total assay volume was 2.03 ml.

Samples were incubated at 25° C. for 60 min., cooled on ice 5 min. and subsequently filtered over Whatman GF/C glass fiber filters with 2.4 ml washes of cold buffer. The filters were then solubilized in 1 ml of NCS at 50° C. for 1 hour. After solubilizaton, the pH was adjusted with 0.1 ml of glacial acetic acid, 10 ml of PCS was added and the samples were counted in a Nuclear Chicago Mark II liquid scintillation counter. This method was used for the following test compounds: Example 4, Example 5, Example 27, Example 28, Example 38, Example 39, and the prior art compound (4).

A modification of this method was used for the following test compounds: Example 16, Example 17, Example 21, Example 22, Example 24, Example 30, Example 31. In this modification, the total assay volume was adjusted to 1.0 ml. Samples were cooled on ice for 10 minutes and dried at 50° C. for 30 minutes, then 10 mls of PCS was added and the samples counted in a liquid scinitillation counter.

The IC$_{50}$ values, the concentration of the test compounds which inhibited $^3$H-Naloxone specific binding to the opiate receptor by 50%, were obtained from log-probit plots of concentration-response curves. D. J. Finney. *Probit Analysis.* Cambridge University Press, London, 1947.

Determination of Selectivity for the Mu and Delta Opiate Receptor

Several subtypes of opiate receptors have been identified. These multiple receptors are thought to mediate the different effects of opiates, e.g., mu receptors are believed to mediate the analgesic activity of opiates. Therefore, the relative affinities of the test compounds for the mu and the delta opiate receptors was determined. The receptor membrane homogenate was prepared using rat brain as previously described in this document. The binding assays for the mu and delta receptors were performed using a modification of the method described by Chang and Cuatrecasas. K.-J. Chang and P. Cuatrecasas. Multiple Opiate receptors: enkephalins and morphine bind to receptors of different specificity. *J. Biol. Chem.* 254, 2610–2618 (1979). The incubation mixtures contained 0.75 ml of homogenate (1 mg protein/ml) and 0.05 ml of $^3$H-Dihydromorphine (final concentration of 0.2 nM) or 0.05 ml $^3$H-(D)-Ala$^2$-(D)-Leu$^5$ enkephalin (final concentration of 0.2 nM). Both the displacer, naloxone, and the test compounds were added in 0.1 ml volumes. Finally, 0.2 ml tris-HCl buffer (pH 7.4 at 25° C.) was added to bring the total volume up to 1 ml. The mixtures were then incubated 60 minutes at 25° C. before filtering.

The IC$_{50}$ values, i.e., the concentration of the test compound that inhibited ligand specific binding to its receptor by 50%, were calculated using log-probit analysis. D. J. Finney. Probit Analysis. Cambridge University Press. London, (1947).

Hypertensive Test

A compound's ability to act as an antihypertensive agent was determined using spontaneous hypertensive rats (SHR). Male SHR were maintained in-house for 1 or more weeks before use and were between 11 and 16 weeks old. The test compound was administered intravenously and the initial mean arterial blood pressure was measured directly via an arterial catheter implanted immediately before administration of the compound. Blood pressure readings were made 5, 10 and 15 minutes after administration of the compound. A dose of test compound was rated active if the mean post-treatment blood pressure of treated rats was significantly lower (P less than 0.05) than that of concurrent placebo controls. Statistical comparisons were made using the unpaired student's t test.

The compounds can be administered in such oral dosage forms as tablets, capsules, pills, powders, granules, suspensions, or solutions. They may also be administered rectally or vaginally, in such forms as suppositories or bougies. They may also be introduced in the form of eyedrops, intraperitoneally, subcutaneously or intramuscularly, using forms known to the pharmaceutical art. In general the preferred form of administration is oral.

An effective but nontoxic quantity of the compound is employed in treatment. The dosage regimen for preventing or treating symptoms by the compounds of this invention is selected in accordance with a variety of factors including the type, age, weight, sex, and medical condition of the mammal, the severity of the symptoms, the route of administration of the particular compound employed. An ordinary skilled physician or veterinarian will readily determine and prescribe the effective amount based on the route of administration of the analgesic agent to prevent or arrest the progress of the condition. In so proceeding, the physician or veterinarian could employ relatively low dosages at first, subsequently increasing the dose until a maximum response is obtained.

The compounds of Formula 1 can also be administered as pharmaceutically acceptable acid addition salts such as the hydrochloride, hydrobromide, hydroiodide, sulfate, phosphate, acetate, propionate, lactate, maleate, malate, succinate, tartrate and the like. Additionally, the compounds of this invention may be administered in a suitable hydrated form.

The compounds of this invention may be prepared by any number of methods known to those skilled in the art. For example, the particular sequence of reactions by which the individual amino acids are joined to form the compounds of Formula 1 is generally not of critical importance, being chosen principally for convenience or for maximum yields. Moreover, the choice of activating reagents and conditions for joining amino acids or small peptides is not limited to those specifically described herein. Peptide intermediates and products of this invention are typically purified by crystallization, where possible, or by column chromatography. Furthermore, where racemic amino acid starting materials are employed, intermediates and products may be separated during column chromatography into diastereomers. The accompanying descriptions and figures are used to illustrate two of the possible methods used to prepare the compounds of this invention.

ROUTE A

Example 1 phenylmethyl [1R-methyl-2-oxo-2-[(3-phenylpropyl)amino]ethyl]carbamate

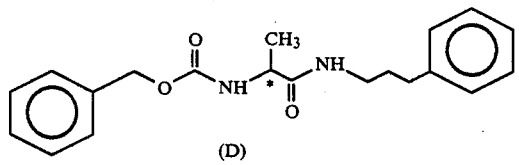

(Z—(D)Ala—PPA)
(Z = carbobenzoxy) (PPA = NH(CH$_2$)$_3$Phenyl)

Z(D)-alanine (9.96 g, 44.5 mmoles) in 100 ml of tetrahydrofuran (THF) was cooled to −30° C. and 5.6 ml (50 mmoles) of N-methylmorpholine (NMM) were added. To this, vigorously stirred solution, 6.6 ml (50 mmoles) of isobutylchloroformate (ICBF) were added dropwise maintaining the temperature between −20° and −30° C. After 5 minutes at this temperature, the stirred reaction was cooled to −40° C. 3-Phenylpropylamine (7.15 ml, 50 mmoles) was added dropwise keeping the temperature at −30° to −40° C. This mixture was stirred for one hour at this temperature and then allowed to warm to room temperature and stand overnight. The mixture was diluted with 200 ml ethyl acetate (EtOAc) and washed twice with 100 ml portions of 0.5N potassium bisulfate (KHSO$_4$). The separated organic extracts were then dried over magnesium sulfate (MgSO$_4$) and stripped of all solvent. The resulting crude product was shaken with Skelly B (hexanes), filtered, and dried to give 15.83 g of crude solid product. This material was crystallized from a mixture of 70 ml isopropanol and 60 ml of water to give 11.39 g (75% yield) of desired produce with a melting point of 92°-93° C. The mother liquor residue was chromatographed eluting with 1% ethanol-methylene chloride (CH$_2$Cl$_2$) to give an additional 2.82 g of product.

Optical rotation: [α]$_D$ +10.9°; (Methanol=MeOH).
Analysis Calcd. for C$_2$H$_{24}$N$_2$O$_3$ (MW 340.42): C, 70.57; H, 7.11; N, 8.23. Found: C, 70.37; H, 7.09; N, 8.24.

EXAMPLE 2

2R-amino-N-(3-phenylpropyl)propanamide

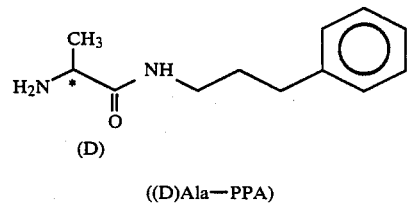

((D)Ala—PPA)

The product in Example 1 above (4.1 g, 12 mmoles) was hydrogenated in 120 ml of ethanol (EtOH) over Pd black catalyst. The hydrogenation was carried out in a Parr Apparatus at room temperature under 60 psi. There was an uptake of 1.0 mole of hydrogen over a 3 hour period. The catalyst was filtered from the solution and all solvent was removed under reduced pressure to produce 2.6 g of the product oil.

Example 3

N-[(1,1-dimethylethoxy)carbonyl]-2,6-dimethyl-DL-tyrosyl-N-(3-phenylpropyl)-D-alaninamide

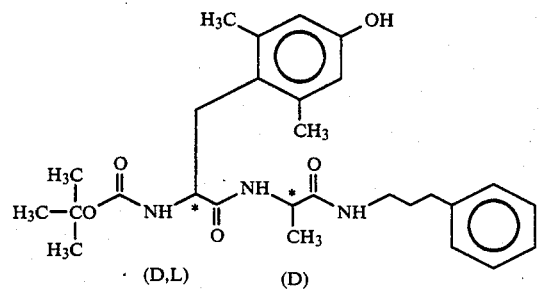

(Boc—(DL)2,6-Me$_2$Tyr—(D)Ala—PPA)
(Boc = t-butoxycarbonyl)

Racemic t-butoxycarbonyl-2,6-dimethyltyrosine (3.09 g, 10 mmoles) was converted to a mixed anhydride at −30° C. in 25 ml of THF as described for Example 1 above. This solution was then cooled to −50° C. and the product of Example 2 (2.5 g, 12 mmoles) dissolved in 20 ml of THF, was added dropwise to the stirred solution. The mixture was allowed to warm to room temperature and stand overnight. The crude product mixture was isolated as described above for the product of Example 1. This material was separated by high performance liquid chromatography (HPLC) using a 0-6% methanol (MeOH)/chloroform (CHCl$_3$) gradient elution to give the two product diastereomers. In a TLC elution system of 10% MeOH/CHCl$_3$, diastereomer F is the faster moving compound while diastereomer S is the slower moving.

Diastereomer F (1.3 g) [α]$_D$−10.8; (MeOH)
Analysis Calcd. for C$_{28}$H$_{39}$N$_3$O$_5$ (MW=497.63): C, 67.58; H, 7.90; N, 8.44. Found: C, 67.65; H, 8.04; N, 8.33.
Diastereomer S (0.84 g) [α]$_D$+60.0°; (MeOH)
Analysis Calcd. for C$_{28}$H$_{39}$N$_3$O$_5$ (M.W.=497.64): C, 67.58; H, 7.90; N, 8.44. Found: C, 67.00; H, 8.02; N, 8.23.

EXAMPLE 4

2,6-dimethyltyrosyl-N-(3-phenylpropyl)-D-alaninamide hydrochloride (fast isomer)

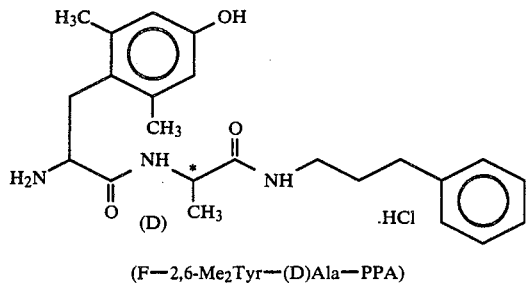

(F—2,6-Me₂Tyr—(D)Ala—PPA)

Diastereomer F from Example 3 was dissolved in 10 ml of acetic acid (HOAc). To this solution was added 10 ml 6N HCl/dioxane. This solution was allowed to stand for one hour at room temperature before all solvent was removed under reduced pressure. The resulting oil was shaken with ether (Et₂O) to produce a white solid. This product was suction filtered, washed with Et₂O and dried under vacuum to yield 0.90 g of the desired product.

$[\alpha]_D$ —76.7; (MeOH)

Analysis Calcd. for $C_{23}H_{31}N_3O_3 \cdot HCl \cdot 2/3H_2O$ (MW=445.99): C, 61.94; H, 7.53; N, 9.42; Cl, 7.95. Found: C, 62.03; H, 7.51; N, 9.39; Cl, 7.86.

EXAMPLE 5

2,6-dimethyltyrosyl-N-(3-phenylpropyl)-D-alaninamide, hydrochloride (slow isomer)

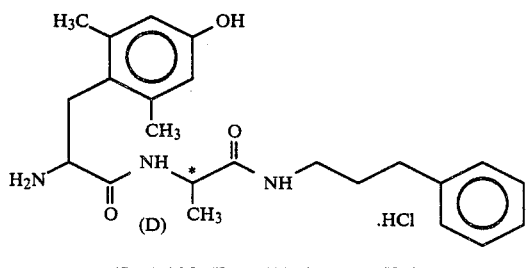

(S—2,6-Me₂Tyr—(D)Ala—PPA.HCl)

Diastereomer S Example 3, (0.84 g, 1.7 mmoles) was deblocked as described in Example 4 to produce 0.55 g of the white powder product. $[\alpha]_D$ +115.0° (MeOH)

Analysis Calcd. for $C_{23}H_{31}N_3O_3 \cdot HCl \cdot H_2O$ (MW=451.99): C, 61.18; H, 7.58; N, 9.30; Cl, 7.84. Found: C, 61.58; H, 7.28; N, 9.24; Cl, 7.89.

(End Route A)

ROUTE B

Example 6

N-[(1,1-dimethylethoxy)carbonyl]-2,6dimethyl-DL-tyrosyl-D-alanine, methyl ester

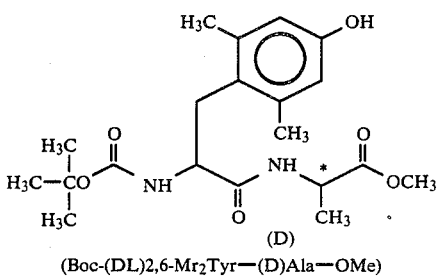

(Boc-(DL)2,6-Mr₂Tyr—(D)Ala—OMe)

Racemic t-butoxycarbonyl 2,6-dimethyltyrosine (3.9 g, 10 mmoles) was dissolved in 30 ml of CH₂Cl₂ by adding 1.12 ml (10 mmoles) of NMM. After bringing this mixture to reflux it was cooled to −30° C. and 1.32 ml (10 mmoles) of IBCF were added to this stirred solution. The temperature was allowed to rise to −15° C. and then lowered to −50° C. (D) alanine methyl ester hydrochloride (1.54 g, 11 mmoles) was added to the solution followed by 1.3 ml (11 mmoles) of NMM. The mixture was allowed to warm to room temperature and stand for 16 hours. The majority of the CH₂Cl₂ was removed under reduced pressure. Ethyl acetate (200 ml) was added and this solution was washed twice with 100 ml portions of 0.5 molar KHSO₄, once with 100 ml of H₂O and dried over MgSO₄. Removal of all solvent gave 3.9 g of the mixture of diastereomers. Recrystallization of this material from Skelly B/CH₂Cl₂ produced 1.6 g (4.2 mmoles) of diastereomer F. Removal of the solvent from the filtrate gave 1.3 g (3.3 mmoles) of diastereomer S contaminated by less than 10% of diastereomer F.

Example 7

2,6-dimethyltyrosyl-D-alanine, methyl ester hydrochloride (fast isomer)

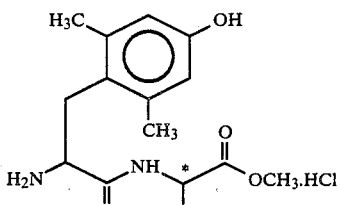

(F—2,6-Me₂Tyr—(D)Ala—OMe.HCl)

The title compound is prepared by the method of Example 4 using diastereomer F from Example 6.

Example 8

2,6-dimethyltyrosyl-D-alanine, methyl ester hydrochloride (slow isomer)

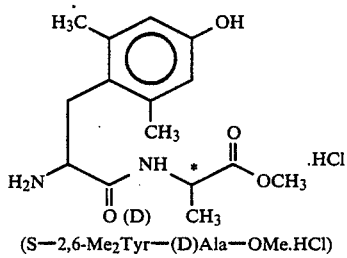

(S—2,6-Me₂Tyr—(D)Ala—OMe.HCl)

The title compound is prepared by the method of Example 4 using diastereomer S from Example 6.

Example 9

N-[(1,1-dimethylethoxy)carbonyl]-2,6-dimethyl-tyrosyl-D-alanine (slow isomer)

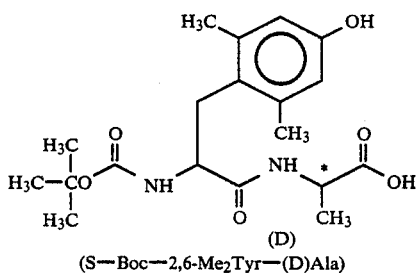

(S—Boc—2,6-Me₂Tyr—(D)Ala)

A 13.0 g (33 mmoles) sample of the title compound of Example 6 (diastereomer S) was dissolved in 50 ml of MeOH. To this was added 50 ml of 1N NaOH. The mixture was stirred for 16 hours, acidified with 0.5N KHSO₄ to pH2 and extracted with EtOAc. The organic layer was washed with brine, dried over MgSO₄, and concentrated to produce 12 g (95%) of the product as a foam. $[\alpha]_D +16.5°$ (CHCl₃)

Analysis Calcd. for C₁₉H₂₈N₂O₆ (MW=380.44): C, 59.99; H, 7.42; N, 7.36. Found: C, 59.19; H, 7.44; N, 7.17.

Example 10

N-[(1,1-dimethylethoxy)carbonyl]-2,6-dimethyl-tyrosyl-D-alanine (fast isomer)

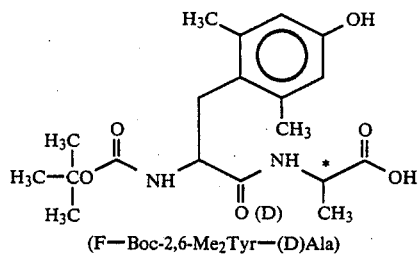

(F—Boc-2,6-Me₂Tyr—(D)Ala)

The title compound was prepared by the methods of Example 9 using diastereomer F of the title compound of Example 6. $[\alpha]_D -21.7$ (CHCl₃)

Example 11

2,6-dimethyltyrosyl-D-alanine, hydrochloride (slow isomer)

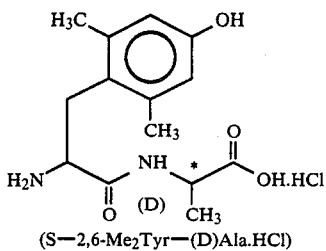

(S—2,6-Me₂Tyr—(D)Ala.HCl)

The title compound is prepared by the methods of Example 4 from diastereomer S of Example 9.

Example 12

2,6-dimethyltyrosyl-D-alanine, hydrochloride (fast isomer)

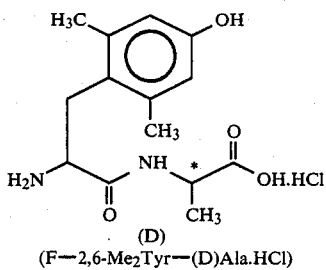

(F—2,6-Me₂Tyr—(D)Ala.HCl)

The title compound is prepared by the methods of Example 4 from the product of Example 10.

Example 13

N-[(1,1-dimethylethoxy)carbonyl]-2,6-dimethyl-tyrosyl-N-(3-phenylpropyl)-D-alaninamide (slow isomer)

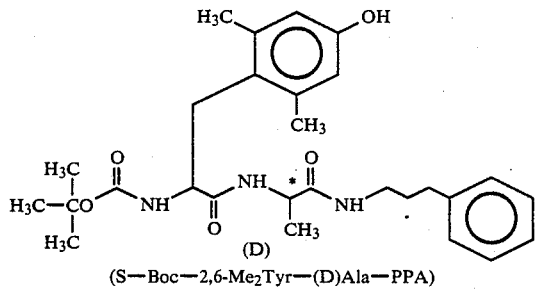

(S—Boc—2,6-Me₂Tyr—(D)Ala—PPA)

A CH₂Cl₂ solution (100 ml) of the title compound from Example 9, (16.6 g, 43.6 mmole) was charged with 4.4 g (43.6 mmoles) of NMM and cooled to −45° C. To this solution was added 5.7 g (43.6 mmole) of IBCF and the mixture warmed to 10° C. The solution was then cooled to −25° C. before adding 7.4 g (54.5 mmole) of 3-phenylpropylamine. After allowing the reaction to warm to room temperature and stand overnight, it was diluted with 300 ml of EtOAc and extracted with three 100 ml portions of 0.5N KHSO₄. The combined aqueous washes were extracted with 100 ml of EtOAc and this extract was combined with the original organic phase. The combined organic was then washed with one 150 ml portion of brine before drying it over Na₂SO₄. All solvent was removed under reduced pressure to give the title product as a foam. This material was chromatographed to give 10 g (46%) of a compound identical to diastereomer S of Example 3.

Example 14

N-[(1,1-dimethylethoxy)carbonyl]-2,6-dimethyl-tyrosyl-N-(3-phenylpropyl)-D-alaninamide (fast isomer)

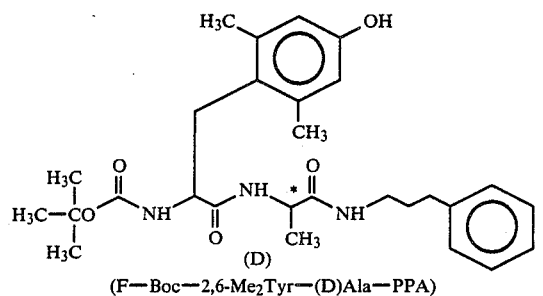

(F—Boc—2,6-Me₂Tyr—(D)Ala—PPA)

The title compound was prepared by the method of Example 13 using the title material of Example 10 and was found to be identical to diastereomer F of Example 3.

Example 15

N-[(1,1-dimethylethoxy)carbonyl]-2-methyl-DL-tyrosyl-N-(3-phenylpropyl)-D-alaninamide (fast and slow isomers)

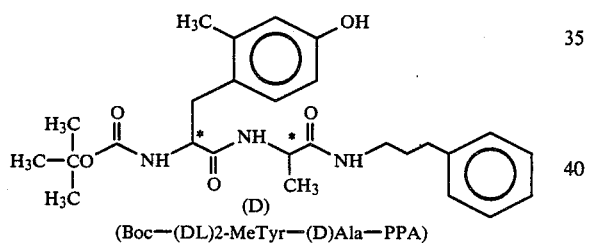

(Boc—(DL)2-MeTyr—(D)Ala—PPA)

The title compounds were prepared and separated using the methods of Example 3 employing racemic t-butoxycarbonyl-2-methyltyrosine in place of t-butoxycarbonyl-2,6-dimethytyrosine.

Diastereomer F [α]$_D$+13.6 (CHCl₃)
Analysis Calcd. for C₂₇H₃₇N₃O₅ (MW=483.61): C, 67.06; H, 7.71; N, 8.69. Found: C, 66.61; H, 7.70; N, 8.66.
Diastereomer S [α]$_D$+27.0 (CHCl₃)
Analysis Calcd. for C₂₇H₃₇N₃O₅ (MW=483.61): C, 67.06; H, 7.71; N, 8.69. Found: C, 66.38; H, 7.68; N, 8.72.

Example 16

2-methyltyrosyl-N-(3-phenylpropyl)-D-alaninamide, hydrochloride (fast isomer)

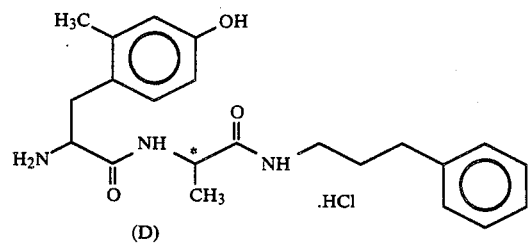

(F—2-MeTyr—(D)Ala—PPA.HCl)

The title compound was prepared by the method of Example 4 from diastereomer F of the title compound of Example 11, Route B. [α]$_D$—23.8 (MeOH)
Analysis Calcd. for C₂₂H₃₀N₃O₃Cl.½H₂O (MW-428.96): C, 61.60; H, 7.30; N, 9.80; Cl, 8.26. Found: C, 62.08; H, 6.99; N, 9.84; Cl, 8.36.

Example 17

2-methyltyrosyl-N-(3-phenylpropyl)-D-alaninamide, hydrochloride (slow isomer)

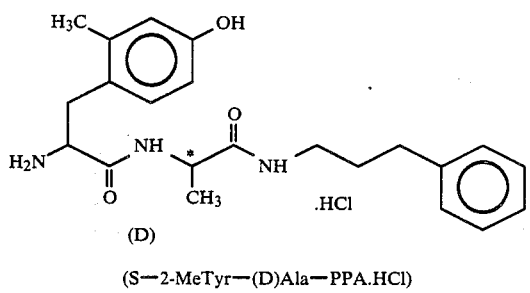

(S—2-MeTyr—(D)Ala—PPA.HCl)

The title compound was prepared by the method of Example 4 from diastereomer 5 of Example 15. [α]$_D$+86.1 (MeOH)
Analysis Calcd. for C₂₂H₃₀N₃O₃Cl.½H₂O (MW=428.96): C, 61.60; H, 7.30; N, 9.80; Cl, 8.26. Found: C, 61.40; H, 7.03; N, 9.80; Cl, 8.05.

Example 18

N-[1,1-dimethylethoxy)carbonyl]-2,3,6-trimethyltyrosyl-N-(3-phenylpropyl)-D-alaninamide, (2-methylpropyl)carbonate (ester), (fast and slow isomers)

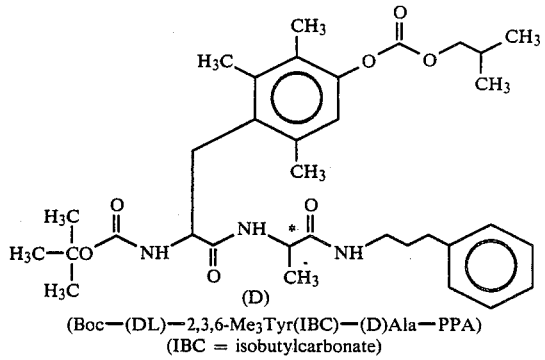

(Boc—(DL)—2,3,6-Me₃Tyr(IBC)—(D)Ala—PPA)
(IBC = isobutylcarbonate)

Racemic t-butoxycarbonyl-2,3,6-trimethyltyrosine (5.0 g, 15.5 mmole), CH₂Cl₂ (100 ml) and molecular sieve #5A (10 g) were combined in a reaction flask. This stirred mixture under an Ar atmosphere was cooled to 0° C. before addition of 3.4 ml (31 mmole) of NMM. After cooling the mixture to −78° C., 4.1 ml (31 mmole) of IBCF were added. The reaction was allowed to warm just to 20° C. before cooling it to −78° C. and adding 3.62 g (15.5 mmole) of 3-phenylpropylamine. The mixture was warmed to room temperature and stirred overnight before filtering the reaction and diluting the filtrate with 250 ml of CH₂Cl₂. This filtrate was extracted with 3×100 ml of 0.5N KHSO₄ and the combined aqueous washes extracted once with a 75 ml portion of CH₂Cl₂. The combined organics were then washed with 100 ml of brine, dried over Na₂SO₄ and stripped of all solvent under reduced pressure. The crude product mixture was chromotographed to provide 1.83 g of diastereomer F, 2.13 g of diastereomer S and 2.30 g of the mixture.

Diastereomer F: $[\alpha]_D+31.2$ (CHCl₃)

Analysis Calcd. for C₃₄H₄₉N₃O₇ (MW=611.80): C, 66.75; H, 8.07; N, 6.87. Found: C, 67.01; H, 8.00; N, 6.75.

Diastereomer S: $[\alpha]_D+5.3$ (CHCl₃)

Analysis Calcd. for C₃₄H₄₉N₃O₇ (MW=611.80): C, 66.75; H, 8.07; N, 6.87. Found: C, 66.93; H, 8.19; N, 6.67.

Example 19

N-[(1,1-dimethylethoxy)carbonyl]-2,3,6-trimethyltyrosyl-N-(3-phenylpropyl)-D-alaninamide (slow isomer)

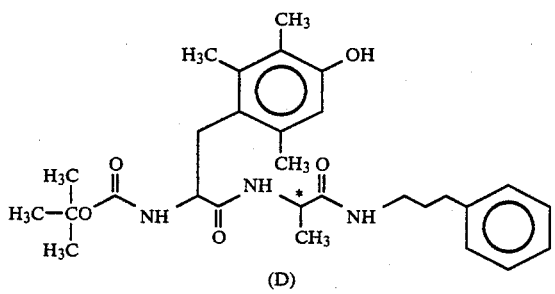

(S—Boc—2,3,6-Me₃Tyr—(D)Ala—PPA)

A 1.6 g (2.6 mmole) sample of the title compound of Example 18, Diastereomer F was dissolved in 40 ml of methanol. To the solution was added 0.36 g (2.6 mmole) of potassium carbonate. The mixture was stoppered and stirred at room temperature for two hours before diluting with 300 ml of CH₂Cl₂ and extracting with 3×100 ml 0.5N KHSO₄. The combined aqueous extracts were then washed with a 75 ml aliquote of CH₂Cl₂. The combined organic fractions were washed with 100 ml of brine, dried over Na₂SO₄, and stripped of all solvent under reduced pressure to yield 1.29 g (96%) of analytically pure diastereomer S.

Diastereomer S $[\alpha]_D+41.8$ (CHCl₃)

Analysis Calcd. for C₂₉H₄₁N₃O₅ (MW=511.68): C, 68,08; H, 8.08; N, 8.21. Found: C, 67.84; H, 8.22; N, 7.89.

Example 20

N-[(1,1-dimethylethoxy)carbonyl]-2,3,6-trimethyltyrosyl-N-(3-phenylpropyl)-D-alaninamide (fast isomer)

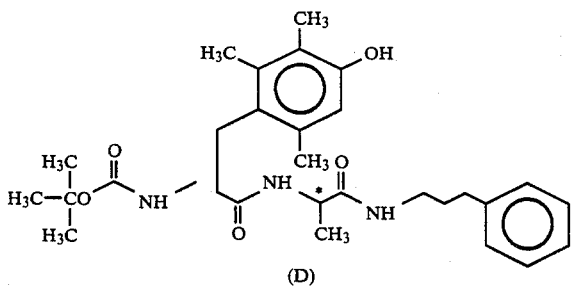

(F—Boc—2,3,6-Me₃Tyr—(D)Ala—PPA)

The title compound was prepared by the method of Example 18, from diastereomer S of the title compound of Example 18. (The TLC relative portions of the title compounds of Example 18 are inverted when converted to the title compounds of Examples 19 and 20)

Diastereomer F: $[\alpha]_D+2.8$ (CHCl₃)

Analysis Calcd. for C₂₉H₄₁N₃O₅ (MW=511.68): C, 68.08; H, 8.08; N, 8.21. Found: C, 68.11; H, 8.11; N, 8.24.

Example 21

2,3,6-trimethyltyrosyl-N-(3-phenylpropyl)-D-alaninamide, hydrochloride (slow isomer)

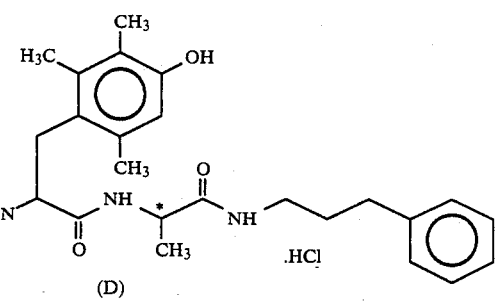

(S—2,3,6-Me₃Tyr—(D)Ala—PPA.HCl)

The title compound was prepared by the method of Example 4 using the title compound of Example 19.

Diastereomer S: $[\alpha]_D+114.0$ (MeOH)

Analysis Calcd. for C₂₄H₃₄N₃O₃Cl.½H₂O (MW=457.03): C, 63.07; H, 7.72; N, 9.20. Found: C, 63.44; H, 7.58; N, 9.08.

Example 22

2,3,6-trimethyltyrosyl-N-(3-phenylpropyl)-D-alaninamide, hydrochloride (fast isomer)

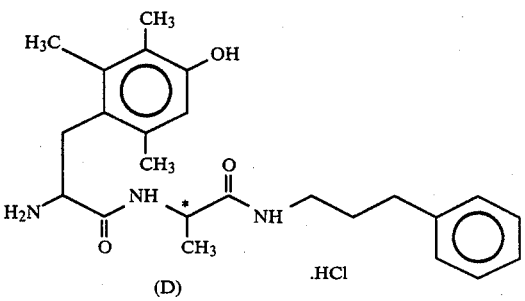

(F—2,3,6-Me₃Tyr—(D)Ala—PPA.HCl)

The title compound was prepared by the method of Example 4 using the title compound of Example 20.

Diastereomer F: $[\alpha]_D+83.4$

Analysis Calcd. for C₂₄H₃₄N₃O₃Cl (MW=448.02): C, 64.34; H, 7.65; N, 9.38. Found: C, 64.23; H, 7.53; N, 9.36.

Example 23

N-[1,1-dimethylethoxy)carbonyl]-2-hydroxy-4,6-dimethyl-DL-phenylalanyl-N-(3-phenylpropyl)-D-alaninamide (diastereomers F and S)

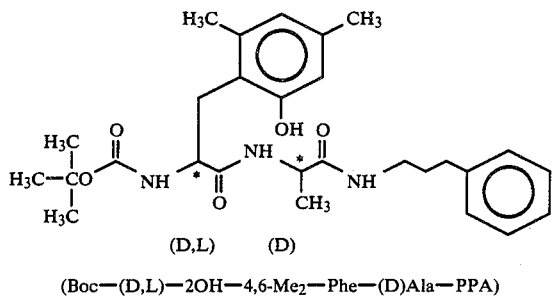

(Boc—(D,L)—2OH—4,6-Me₂—Phe—(D)Ala—PPA)

The title compounds were prepared and separated by the methods of Example 3 using racemic t-butoxycarbonyl-2-hydroxy-4,6-dimethylphenylalanine in place of t-butoxycarbonyl-2,6-dimethyltyrosine. The diastereomeric mixture was not separated.

Diastereomer F and S:

Analysis Calcd. for $C_{28}H_{39}N_3O_5$ (MW=497.63): C, 67.58; H, 7.90; N, 8.44. Found: C, 67.17; H, 7.86; N, 8.42.

Example 24

2-hydroxy-4,6-dimethyl-DL-phenylalanyl-N-(3-phenylpropyl)-D-alaninamide, hydrochloride

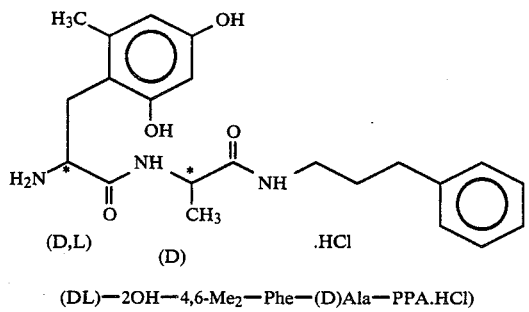

(DL)—2OH—4,6-Me₂—Phe—(D)Ala—PPA.HCl)

The title compound was prepared by the method of Example 4 from the title compound of Example 23.

Analysis Calcd. for $C_{23}H_{32}N_3O_5Cl.\frac{1}{2}H_2O$ (MW=452.00):

Diastereomer F and S: C, 61.11; H, 7.60; N, 9.30. Found: C, 61.21; H, 7.23; N, 9.31.

Example 25

2R-amino-N-(3-cyclohexylpropyl)propanamide

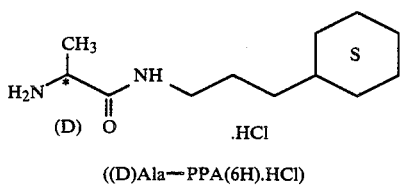

((D)Ala—PPA(6H).HCl)

A 2.4 g (10 mmole) sample of the title compound of Example 2 as its hydrochloride salt was dissolved in THF (40 ml) and MeOH (30 ml) and hydrogenated in a standard Parr apparatus using 0.4 g of 5% Rh on carbon as catalyst. The reaction was run at a pressure of 60 psi and at a temperature of 60° C. After the theoretical amount of hydrogen was taken up, the catalyst was removed by filtration and all solvent removed under reduced pressured. The product, obtained as a hygroscopic light pink glass, was used without further purification.

Example 26

N-[(1,1-dimethylethoxy)carbonyl]-2,6-dimethyltyrosyl-N-(3-cyclohexylpropyl)-D-alaninamide, (2-methylpropyl)carbonate (ester), (fast and slow isomers)

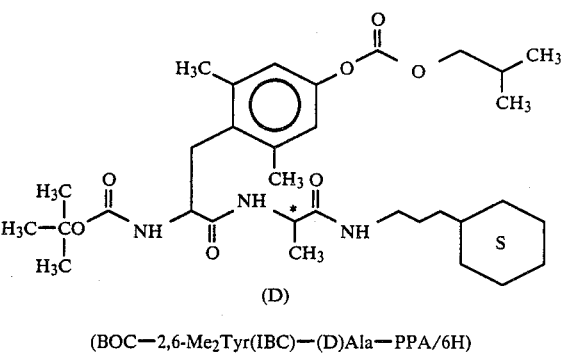

(BOC—2,6-Me₂Tyr(IBC)—(D)Ala—PPA/6H)

The title compounds were prepared and separated using the methods of Example 18 and the title compound of Example 25 in place of 3-phenylpropylanine. One additional equivalent of NMM was also used to neutralize the extra equivalent of HCl introduced with the title compound of Example 25.

Diastereomer F $[\alpha]_D +43.6$ (MeOH)

Analysis Calcd. for $C_{33}H_{53}N_3O_7$ (MW=603.82): C, 65.64; H, 8.85; N, 6.96. Found: C, 65.63; H, 8.91; N, 6.79.

Diastereomer S $[\alpha]_D = 5.0$ (MeOH)

Analysis Calcd. for $C_{33}H_{53}N_3O_7$ (MW=603.82): C, 65.64; H, 8.85; N, 6.96. Found: C, 65.65; H, 8.86; N, 6.82.

Example 27

2,6-dimethyltyrosyl-N-(3-cyclohexylpropyl)-D-alaninamide, (2-methylpropyl)carbonate (ester), (fast isomer)

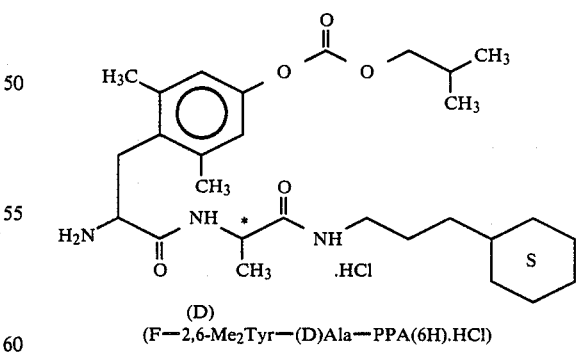

(F—2,6-Me₂Tyr—(D)Ala—PPA(6H).HCl)

The title compound was prepared by the method of Example 4 for diastereomer F of the title compound from Example 26.

Diastereomer F: $[\alpha]_D$ 103.0 (MeOH)

Analysis Calcd. for $C_{28}H_{46}N_3O_5Cl.\frac{1}{2}H_2O$ (MW=549.17): C, 61.24; H, 8.63; N, 7.65. Found: C, 61.49; H, 8.38; N, 7.61.

Example 28

2,6-dimethyltyrosyl-N-(3-cyclohexylpropyl)-D-alaninamide, (2-methylpropyl)carbonate (ester), (slow isomer)

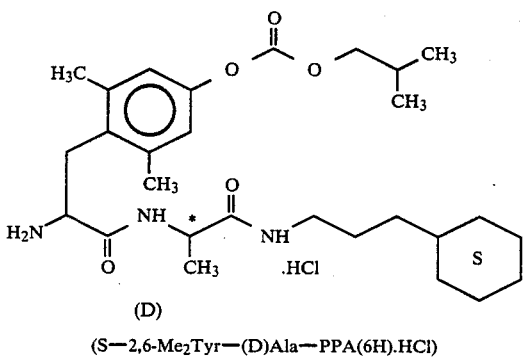

(S—2,6-Me2Tyr—(D)Ala—PPA(6H).HCl)

The title compound was prepared by the method of Example 4 from diastereomer S of the title compound from Example 26.

Diastereomer S: $[\alpha]_D -56.9$ (MeOH)

Analysis Calcd. for $C_{28}H_{46}N_3O_5Cl$ (540.16): C, 62.26; H, 8.58; N, 7.78. Found: C, 62.02; H, 8.70; N, 7.65.

Example 29

N-[1,1-dimethylethoxy)carbonyl]-2,6-dimethyl-DL-tyrosyl-N-(3-cyclohexylpropyl)-D-alaninamide

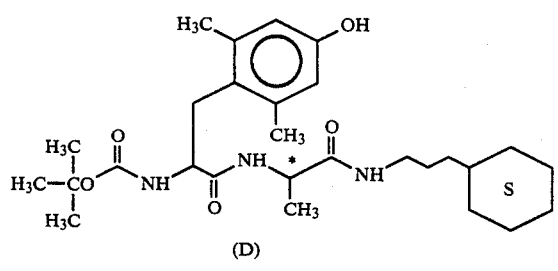

(Boc—(DL)2,6-Me2Tyr—(D)Ala—PPA(6H))

The title compounds were prepared by the method of Example 19 from the title compound of Example 26 as its mixture of diastereomers F and S. The product diastereomers were chromatographically separated as described in Example 3.

Diastereomer F $[\alpha]_D +2.7$ (MeOH)

Analysis Calcd. for $C_{28}H_{45}N_3O_5Cl$ (503.15): C, 66.77; H, 9.00; N, 8.34. Found: C, 66.75; H, 9.07; N, 8.24

Diastereomer S $[\alpha]_D +61.2$ (MeOH)

Analysis Calcd. for $C_{28}H_{45}N_3O_5Cl$ (503.15): C, 66.77; H, 9.00; N, 8.34. Found: C, 66.98; H, 9.13; N, 8.32

Example 30

2,6-dimethyltyrosyl-N-(3-cyclohexylpropyl)-D-alaninamide, hydrochloride (fast isomer)

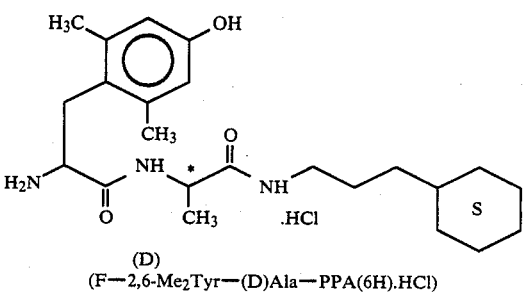

(F—2,6-Me2Tyr—(D)Ala—PPA(6H).HCl)

The title compound was prepared by the method of Example 4 from diastereomer F of the title compound from Example 29.

Diastereomer F: $[\alpha]_D -66.4$ (MeOH)

Analysis Calcd. for $C_{23}H_{38}N_3O_3Cl.\frac{1}{2}H_2O$ (MW=449.05): C, 61.52; H, 8.75; N, 9.35. Found: C, 61.23; H, 8.59; N, 9.31.

Example 31

2,6-dimethyltyrosyl-N-(3-cyclohexylpropyl)-D-alaninamide, hydrochloride (slow isomer)

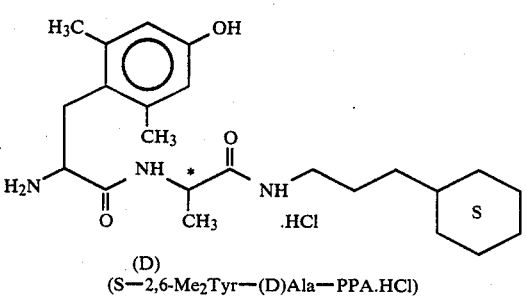

(S—2,6-Me2Tyr—(D)Ala—PPA.HCl)

The title compound was prepared by the method of Example 4 using diastereomer S of the title compound of Example 29.

Diastereromer S: $[\alpha]_D +116.5$ (MeOH)

Analysis Calcd. for $C_{23}H_{38}N_3O_3Cl$ (MW=440.04): C, 60.31; H, 8.80; N, 9.18. Found: C, 60.86; H, 8.48; N, 9.24.

Example 32

2-[3-(2,6-dimethylphenyl)-2-propenyl]-1H-isoindole-1,3(2H)-dione

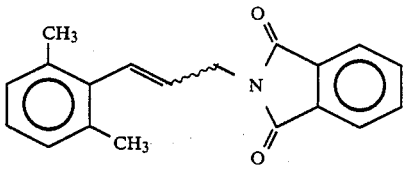

A mixture 9.3 g (50 mmole) of 2-bromo-m-xylene, 15.0 g (80 mmole) of N-allylphthalimide, 0.56 (2.5 mmole) of paladium acetate and 1.44 (5.5 mmole) of triphenylphosphine were dissolved in 111 ml of triethylamine. The solution was placed in a sealed container and heated at 100° C. for 24 hours. The reaction was

Example 33

2-[3-(2,6-dimethylphenyl)propyl]-1H-isoindole-1,3(2H)-dione

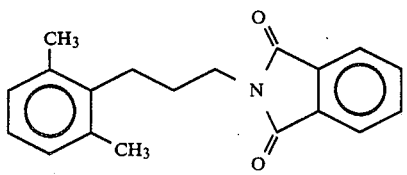

The title compound of Example 32 (10 g, 34 mmole) dissolved in 120 ml of THF and 100 ml of MeOH was reduced in a standard Parr hydrogenation apparatus using 1 g of 5% Pd/C as catalyst. The reaction was run at room temperature under a pressure of 5 psi for 24 hours. The residue after removing all solvent under reduced pressure was chromotographed to yield the pale yellow crystalline product which was recrystallized from Skelly B. The melting point was 92°–93.5° C.

Analysis Calcd. for $C_{19}H_{19}NO_2$ (MW=293.36): C, 77.79; H, 6.53; N, 4.77. Found: C, 77.74; H, 6.64; N, 4.66.

Example 34

2,6-dimethylbenzenepropanamine

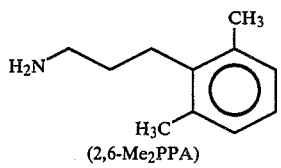

(2,6-Me₂PPA)

A 10 g (34.4 mmole) sample of the title compound of Example 33 was refluxed for 2 hours in 150 ml of ethanol containing 1.2 g (36.7 mmole) of 97% hydrazine. After concentrating the solution, the white crystalline residue was mixed with 100 ml of 10% NaOH and 100 ml of ether. The aqueous phase was separated and extracted with another 100 ml portion of ether. The combined ether extracts were than washed with water, dried over MgSO₄ and stripped of all solvent under reduced pressure to yield 3.3 g (59%) of the product as an oil. This material was used without further purification.

Example 35

N-[(1,1-dimethylethoxy)carbonyl]-N-[3-(2,6-dimethylphenyl)propyl]-D-alaninamide

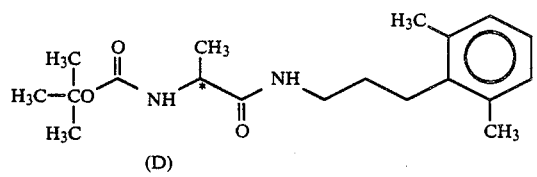

(Boc—(D)Ala—2,6-Me₂PPA)

The title compound was prepared by the method of Example 1 using BOC-(D)Ala in place of Z-(D)Ala and the product of Example 34 in place of 3-phenylpropylamine.

Analysis Calcd. for $C_{19}H_{30}N_2O_3$ (MW=334.46): C, 68.23; H, 9.04; N, 8.38. Found: C, 67.87; H, 9.04; N, 8.40

Example 36

2R-amino-N-[3-(2,6-dimethylphenyl)propyl]propanimide, hydrochloride

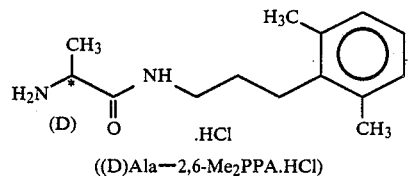

((D)Ala—2,6-Me₂PPA.HCl)

The title compound was prepared by the method of Example 4 using the title compound of Example 35.

Example 37

N-[1,1-dimethylethoxy)carbonyl]-(2,6-dimethyl-tyrosyl N-(3-(2,6-dimethylphenyl)propyl]-D-alaninamide, (fast and slow isomers)

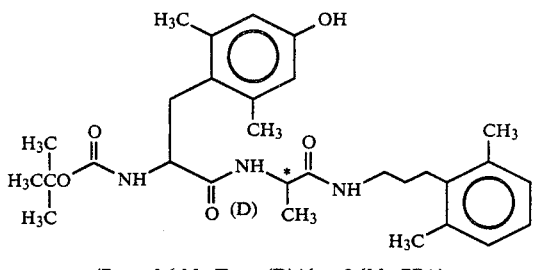

(Boc—2,6-Me₂Tyr—(D)Ala—2,6Me₂PPA)

The title compounds were prepared and their diastereomers separated by the method of Example 3 using the title compound of Example 36 in place of 2-R-Amino-N-(3-phenylpropyl)propanamide and an additional equivalent of NMM to neutralize the extra equivalent of HCl.

Diastereomer F $[\alpha]_D$+2.6 (CHCl₃)

Analysis Calcd. for $C_{30}H_{43}N_3O_5$ (MW 525.69): C, 68.54; H, 8.24; N, 7.99. Found: C, 67.87; H, 8.14; N, 7.73

Diastereomer S $[\alpha]_D$+35.7 (CHCl₃)

Analysis Calcd. for $C_{30}H_{43}N_3O_5$ (MW 525.69): C, 68.54; H, 8.24; N, 7.99. Found: C, 68.39; H, 8.21; N, 7.88

Example 38

2,6-dimethyltyrosyl-N-[3-(2,6-dimethylphenyl)propyl]-D-alaninamide hydrochloride (fast isomer)

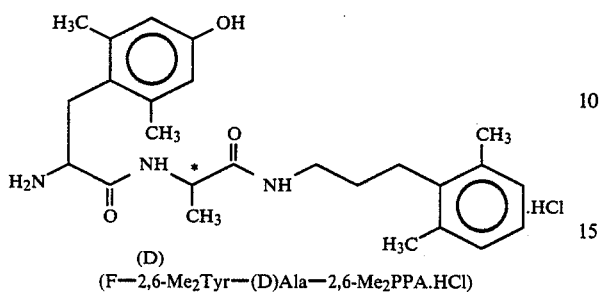

(F—2,6-Me$_2$Tyr—(D)Ala—2,6-Me$_2$PPA.HCl)

The title compound was prepared by the method of Example 4 using the F diastereomer of the title compound of Example 37.

Diastereomer F: $[\alpha]_D -65.0$ (MeOH)

Analysis Calcd. for C$_{25}$H$_{36}$N$_3$O$_3$Cl.½H$_2$O (MW 471.04): C, 63.74; H, 7.93; N, 8.92. Found: C, 63.97; H, 7.60; N, 8.75.

Example 39

2,6-dimethyltyrosyl-N-[3-(2,6-dimethylphenyl)propyl]-D-alaninamide, hydrochloride (slow isomer)

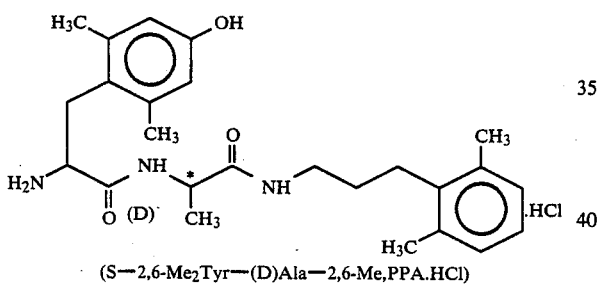

(S—2,6-Me$_2$Tyr—(D)Ala—2,6-Me,PPA.HCl)

The title compound was prepared by the method of Example 4 using the S diastereomer of the title compound of Example 37.

Diastereomer S: $[\alpha]_D +97.4$ (MeOH)

Analysis Calcd. for C$_{25}$H$_{36}$N$_3$O$_3$Cl.½H$_2$O (MW 471.04): C, 63.74; H, 7.93; N, 8.92. Found: C, 64.04; H, 7.71; N, 8.74.

Example 40

N-[(1,1-dimethylethoxy)carbonyl]-(2,6-dimethyltyrosyl-N-(2-phenylethyl)-D-alaninamide (slow isomer)

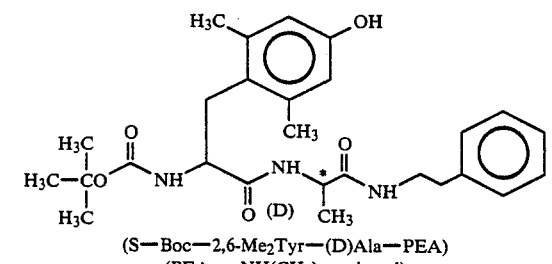

(S—Boc—2,6-Me$_2$Tyr—(D)Ala—PEA)
(PEA = NH(CH$_2$)$_3$—phenyl)

The title compound was prepared by the method of Example 13 using 2-phenylethylamine in place of 3-phenylpropylamine.

Diastereomer S: $[\alpha]_D +47.1$ (MeOH)

Analysis Calcd. for C$_{27}$H$_{37}$N$_3$O$_5$ (MW=483.61): C, 67.06; H, 7.71; N, 8.69. Found: C, 66.67; H, 7.72; N, 8.60

Example 41

2,6-dimethyltyrosyl-N-(2-phenylethyl)-D-alaninamide, hydrochloride (slow isomer)

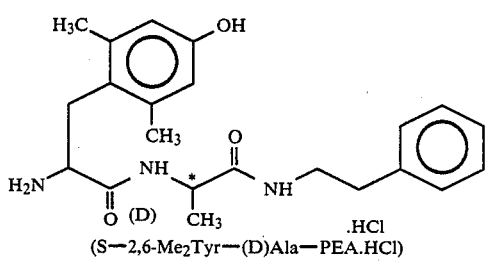

(S—2,6-Me$_2$Tyr—(D)Ala—PEA.HCl)

The title compound was prepared by the method of Example 4 from the title compound of Example 40.

Diasteromer S: $[\alpha]_D +125.0$ (MeOH)

Analysis Calcd. for C$_{22}$H$_{30}$N$_3$O$_3$Cl.½H$_2$O (MW 428.96): C, 61.60; H, 7.30; N, 9.80. Found: C, 61.96; H, 7.35; N, 9.75.

Example 42

N-[(1,1-dimethylethoxy)carbonyl]-(2,6-dimethyltyrosyl)-N-(4-phenylbutyl)-D-alaninamide (slow isomer)

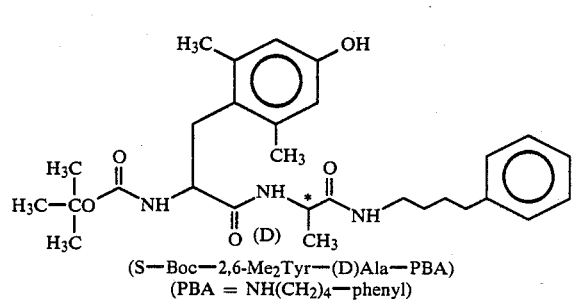

(S—Boc—2,6-Me$_2$Tyr—(D)Ala—PBA)
(PBA = NH(CH$_2$)$_4$—phenyl)

The title compound was prepared by the method of Example 13 using 4-phenylbutylamine in place of 3-phenylpropylamine.

Diastereomer S: $[\alpha]_D +43.3$ (CHCl$_3$)

Analysis Calcd. for C$_{29}$H$_{41}$N$_3$O$_5$ (MW 511.66): C, 68.08; H, 8.08; N, 8.21. Found: C, 67.23; H, 8.05; N, 7.92

Example 43

SC 41473

2,6-dimethyltyrosyl-N-(4-phenylbutyl)-D-alaninamide, hydrochloride (slow isomer)

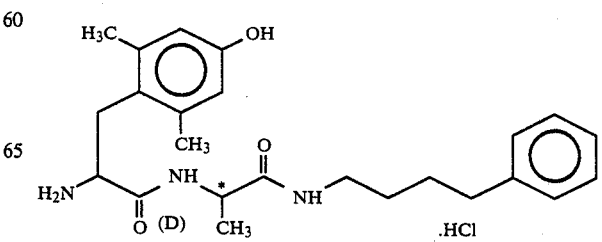

-continued (S—2,6-Me₂Tyr—(D)Ala—PBA.HCl)

The title compound was prepared by the method of Example 4 from the title compound of Example 42.

Diastereomer S: [α]_D + 107.9 (CHCl₃)

Analysis Calcd. for C₂₃H₃₄N₃O₃Cl (MW=448.00): C, 64.34; H, 7.65; N, 9.38. Found: C, 64.17; H, 7.91; N, 9.38.

Example 44 phenylmethyl [1,1-dimethyl-oxo-2-[(3-phenylpropyl)amino]ethyl]carbamate

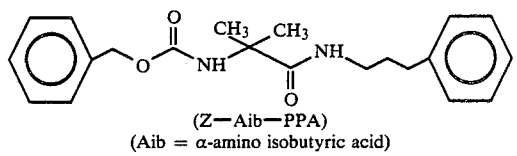

(Z—Aib—PPA)
(Aib = α-amino isobutyric acid)

The title material was prepared by the method of Example 1 using Z α-aminoisobutyric acid in place of Z-(D)alanine and was used without further purification after crystallization from cyclohexane; mp=84°–92° C.

Analysis calcd. for C₂₁H₂₆N₂O₃ (MW=354.45): C, 71.16; H, 7.39; N, 7.90. Found: C, 71.33; H, 7.40; N, 7.91.

Example 45

2-amino-2-methyl-N-(3-phenylpropyl)propanamide

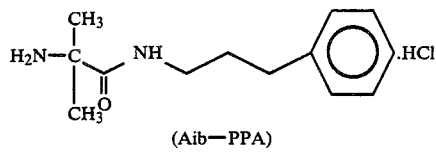

(Aib—PPA)

The title compound was prepared by the method of Example 2 using Z-Aib-PPA in place of Z-(D)ARa-PPA. After removing all solvent the product was used without purification.

Example 46

N-[(1,1-dimethylethoxy)carbonyl]-2,6-dimethyl-DL-tryrosyl-2-methyl-N-(3-phenylpropyl)alaninamide

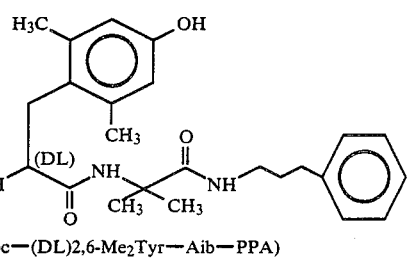

(Boc—(DL)2,6-Me₂Tyr—Aib—PPA)

The title compound was prepared by the method of Example 3 using Aib-PPA in place of (D)Ala-PPA and purified by low pressure chromotography (LPC) eluting with a gradient system of 2–5% MeOH/CHCl₃.

Anal. Calcd. for: C₂₉H₄₁N₃O₅ (MW=511.66): C, 68.08; H, 8.08; N, 8.22. Found: C, 67.57; H, 8.08; N, 8.12.

Example 47

2,6-dimethyl-DL-tyrosyl-2-methyl-N-(3-phenylpropyl)alaninamide

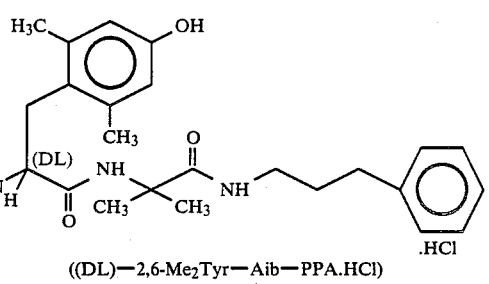

((DL)—2,6-Me₂Tyr—Aib—PPA.HCl)

The title compound was prepared using the method of Example 4.

Analysis Calcd. for C₂₄H₃₄N₃O₃Cl.½H₂O (MW=457.01): C, 63.07; H, 7.74; N, 9.20. Found: C, 63.11; H, 7.43; N, 8.98.

Example 48

N-[(1,1-dimethylethoxy)carbonyl]-2,6-dimethyl-L-tyrosyl-2-methyl-N-(3-phenylpropyl)alaninamide

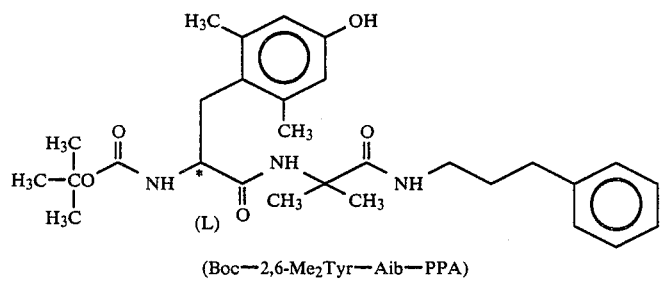

(Boc—2,6-Me₂Tyr—Aib—PPA)

The title compound was prepared by the method of Example 3 from the title compound of Example 45 and Boc-2,6-Me₂Tyr obtained as described by Abersh et al. (H., Abersh, C., Niemann, Biochemistry 2 (1963) 947) which had been converted to its Boc derivative by standard procedures. [α]_D + 25.6; (CHCl₃)

Analysis Calcd. for $C_{29}H_{41}N_3O_5 \cdot \frac{1}{4}H_2O$ (MW=516.18): C, 67.48; H, 8.10; N, 8.14. Found: C, 67.74; H, 8.07; N, 7.77.

Example 49

2,6-dimethyl-L-tyrosyl-2-methyl-N-(3-phenylpropyl)alaninamide, monohydrochloride

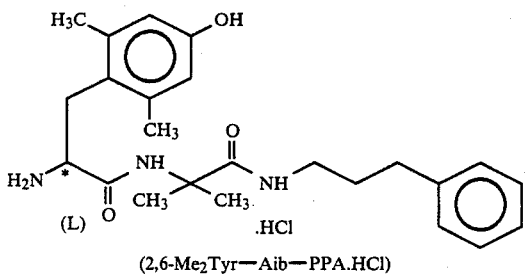

(2,6-Me₂Tyr—Aib—PPA.HCl)

The title compound was prepared by the method of Example 4 from the title compound of Example 48.
$[\alpha]_D$+76.1; (MeOH)
Analysis Calcd. for $C_{24}H_{34}N_3O_3Cl \cdot H_2O$ (MW=466.03): C, 61.85; H, 7.79; N, 9.02; Cl, 7.60. Found: C, 62.21; H, 7.47; N, 8.95; Cl, 7.98.

Example 50

N-[(1,1-dimethylethoxy)carbonyl]-2,6-dimethyl-D-tyrosyl-2-methyl-N-(3-phenylpropyl)alaninamide

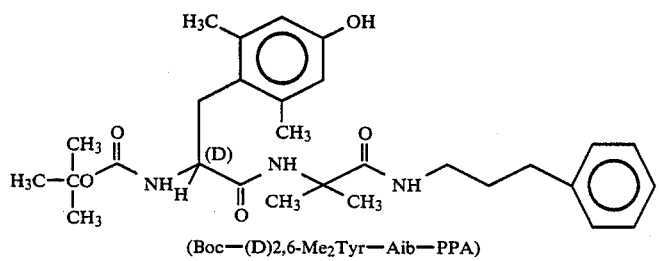

(Boc—(D)2,6-Me₂Tyr—Aib—PPA)

The title material is prepared by the method of Example 3 using Boc-(D)2,6-Me₂Tyr in place of its (L) enanteomer.

Example 51

2,6-dimethyl-D-tyrosyl-2-methyl-N-(3-phenylpropyl)alaninamide, hydrochloride

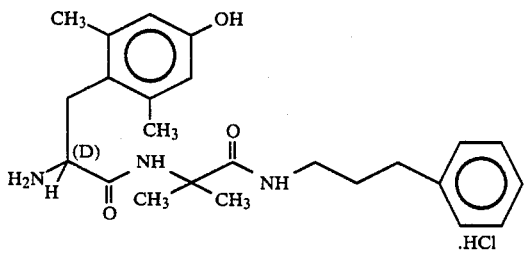

((D)2,6-Me₂Tyr—Aib—PPA.HCl)

The title compound is prepared by the method of Example 4 from the title compound of Example 50.

Example 52

1,1-dimethylethyl[2-oxo-2-[(3-phenylpropyl)amino]ethyl]carbamate

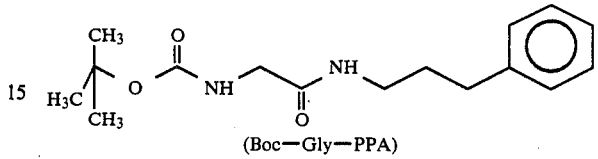

(Boc—Gly—PPA)

The title compound was prepared by the method of Example 1 using Boc-glycine in place of Z-(D)alanine and was used without purification after the initial reaction work-up.

Example 53

2-amino-N-(3-phenylpropyl)acetamide, monohydrochloride

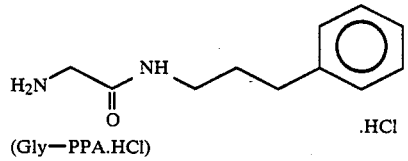

(Gly—PPA.HCl)

The title compound was prepared from the product of Example 52 by the method of Example 4.

Analysis Calcd. for $C_{11}H_{17}N_2OCl$ (MW=228.73): C, 57.73; H, 7.49; N, 12.25. Found: C, 57.43; H, 7.35; N, 12.21.

Example 54

N-[(1,1-dimethylethoxy)carbonyl]-2,6-dimethyl-DL-tyrosyl-N-(3-phenylpropyl)glycinamide

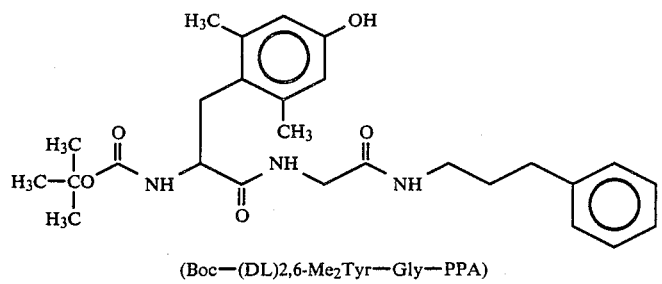

(Boc—(DL)2,6-Me₂Tyr—Gly—PPA)

The title compound was prepared by the method of Example 3 using the title product of Example 53 in place of (D)Ala-PPA and an additional equivalent of NMM to neutralize the additional equivalent of HCl. The product was purified by pressure liquid chromatography (PLC) eluting with 1-7% ethanol (EtOH)/CHCl₃.

Analysis Calcd. for $C_{27}H_{37}N_3O_5$ (MW=483.62): C, 67.06; H, 7.71; N, 8.69. Found: C, 66.77; H, 7.70; N, 9.00.

Example 55

2,6-dimethyl-DL-tyrosyl-N-(3-phenylpropyl)glycinamide, monohydrochloride

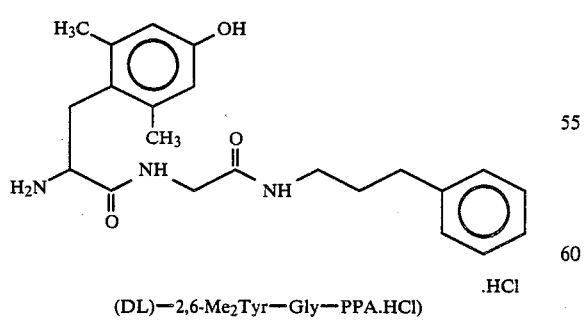

(DL)—2,6-Me₂Tyr—Gly—PPA.HCl)

The title compound was prepared by the method of Example 4 using the title product of Example 54.

Analysis Calcd. for $C_{22}H_{30}N_3O_3Cl \cdot \frac{1}{4}H_2O$ (MW=424.47): C, 62.25; H, 7.24; N, 9.90. Found: C, 62.19; H, 7.06; N, 9.81.

Example 56

N-[(1,1-dimethylethoxy)carbonyl]-2,6-dimethyl-DL-tyrosyl-N-(3-phenylpropyl)glycinamide, (2-methylpropyl)carbonate (ester)

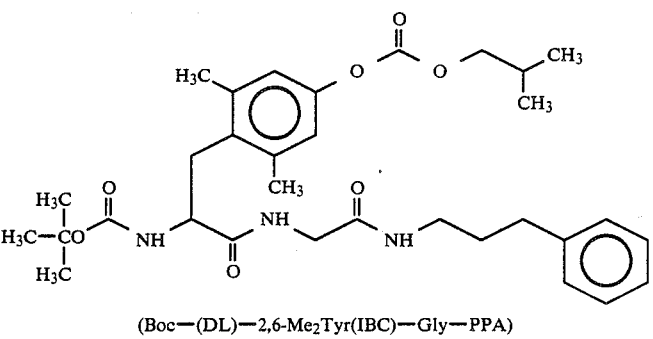

(Boc—(DL)—2,6-Me₂Tyr(IBC)—Gly—PPA)

The title compound was isolated from the reaction mixture of Example 54 by PLC eluting with 1-7% EtOH/CHCl₃.

Analysis Calcd. for $C_{32}H_{45}N_3O_7$ (MW=583.73): C, 65.84; H, 7.70; N, 7.20. Found: C, 65.84; H, 7.60; N, 7.12.

Example 57

2,6-dimethyl-DL-tyrosyl-N-(3-phenylpropyl)glycinamide, (2-methylpropyl)carbonate (ester), monohydrochloride

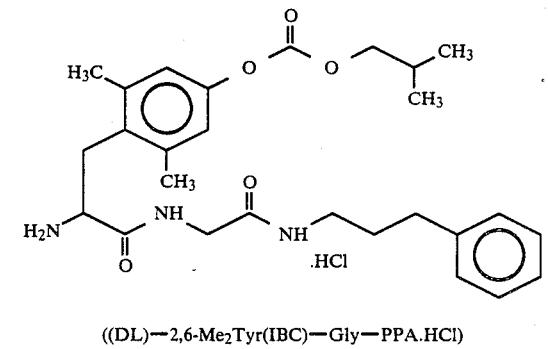

((DL)—2,6-Me₂Tyr(IBC)—Gly—PPA.HCl)

The title compound was prepared from the product of Example 56 by the method of Example 4.

Analysis Calcd. for $C_{27}H_{38}N_3O_5Cl \cdot \frac{1}{2}H_2O$ (MW=529.09): C, 61.29; H, 7.43; N, 7.94. Found: C, 61.56; H, 7.29; N, 7.98.

Example 58

N-[(1,1-dimethylethoxy)carbonyl]-2,4-dimethyl-3-[[(2-methylpropoxy)carbonyl]oxy]-DL-phenylalanyl-N-(3-phenylpropyl)-D-alaninamide

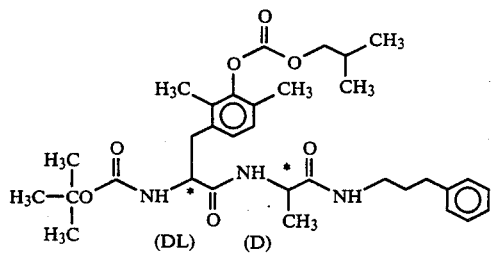

(BOC—(DL)—2,4-Me₂-meta-Tyr(IBC)—(D)Ala—PPA)

The title compound was prepared by the method of Example 18 using racemic t-butoxycarbonyl-2,4-dimethylmetatyrosine in place of racemic t-butoxycarbonyl-2,3,6-trimethyltyrosine. The product was obtained after PLC chromatography as a mixture of diastereomers and was used without further purification.

Example 59

N-[(1,1-dimethylethoxy)carbonyl]-3-hydroxy-2,4-dimethyl-DL-phenylalanyl-N-(3-phenylpropyl)-D-alaninamide

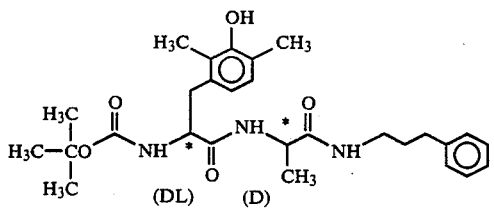

(Boc—(DL)—2,4-Me₂-meta-Tyr—(D)Ala—PPA)

The title compound was prepared by the method of Example 19 from the title product of Example 58.
Analysis Calcd. for $C_{28}H_{39}N_3O_5 \cdot \frac{1}{4}H_2O$ (MW=502.15): C, 66.97; H, 7.92; N, 8.36. Found: C, 66.97; H, 7.88; N, 8.39.

Example 60

3-hydroxy-2,4-dimethyl-DL-phenylalanyl-N-(3-phenylpropyl)-D-alaninamide, monohydrochloride

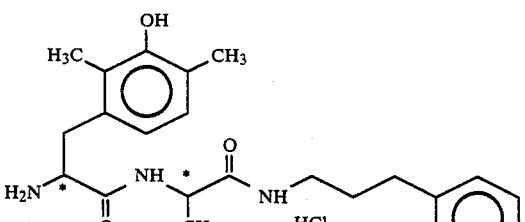

((DL)—2,4-Me₂-meta-Tyr—(D)Ala—PPA.HCl)

The title compound was prepared from the title product of Example 59 by the method of Example 4.
$[\alpha]_D + 19.2$; (MeOH).

Analysis Calcd. for $C_{23}H_{32}N_3O_3Cl \cdot \frac{3}{4}H_2O$ (MW=447.50): C, 61.73; H, 7.54; N, 9.39. Found: C, 61.74; H, 7.20; N, 9.43.

Example 61 phenylmethyl[1S-methyl-2-oxo-2-[(3-phenylpropyl)amino]ethyl]carbamate

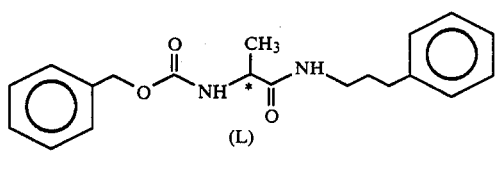

(Z—Ala—PPA)

The title compound was prepared by the method of Example 1 using Z-alanine in place of Z(D)-alanine.
$[\alpha]_D - 11.8$; (MeOH)
Analysis Calcd. for $C_{20}H_{24}N_2O_3$ (MW=340.43): C, 70.57; H, 7.11; N, 8.23. Found: C, 70.56; H, 7.15; N, 8.18.

Example 62

2S-amino-N-(3-phenylpropyl)propanamide

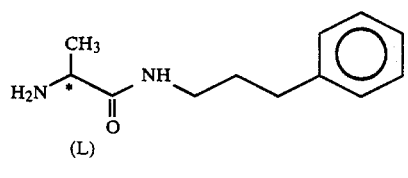

(Ala—PPA)

The title compound was prepared by the method of Example 2 from the product of Example 61.
$[\alpha]_D + 5.6$; (MeOH)
Analysis Calcd. for $C_{12}H_{18}N_2O \cdot \frac{1}{4}H_2O$ (MW=210.80): C, 68.37; H, 8.85; N, 13.29. Found: C, 68.66; H, 8.60; N, 12.36.

Example 63

N-[(1,1-dimethylethoxy)carbonyl]-2,6-dimethyl-DL-tyrosyl-N-(3-phenylpropyl)-L-alaninamide

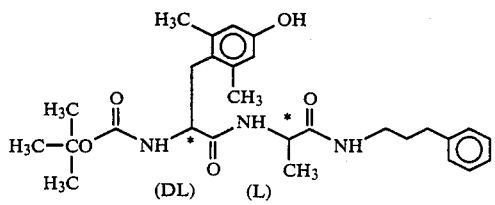

(Boc—(DL)2,6-Me₂Tyr—Ala—PPA)

The title mixture of diastereomers were prepared and separated by the method of Example 3 using the product of Example 62.
Diastereomer F $[\alpha]_D - 1.0$; (CHCl₃)
Analysis Calcd. for $C_{28}H_{39}N_3O_5$ (MW=497.64): C, 67.58; H, 7.90; N, 8.44. Found: C, 67.77; H, 8.13; N, 8.23.
Diastereomer S $[\alpha]_D - 3.92$; (CHCl₃)
Analysis Calcd. for $C_{28}H_{39}N_3O_5$ (MW=497.64): C, 67.58; H, 7.90; N, 8.44. Found: C, 67.33; H, 8.00; N, 8.08.

Example 64

2,6-dimethyltyrosyl-N-(3-phenylpropyl)-L-alaninamide, monohydrochloride (fast isomer)

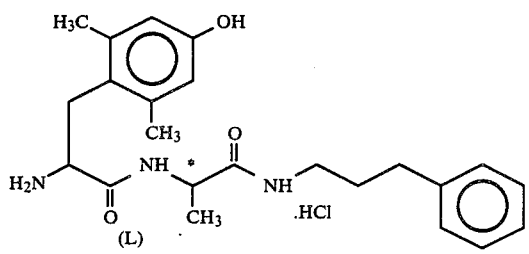

(F—2,6-Me₂Tyr—Ala—PPA.HCl)

The title compound was prepared by the method of Example 4 from diastereomers F of Example 63.

$[\alpha]_D$ +71.6; (MeOH)

Analysis Calcd. for $C_{23}H_{32}N_3O_3Cl \cdot \frac{1}{4}H_2O$ (438.49): C, 63.00; H, 7.47; N, 9.58; Cl, 8.08. Found: C, 63.21; H, 7.48; N, 9.37; Cl, 8.16.

Example 65

2,6-dimethyltyrosyl-N-(3-phenylpropyl)-L-alaninamide, monohydrochloride (slow isomer)

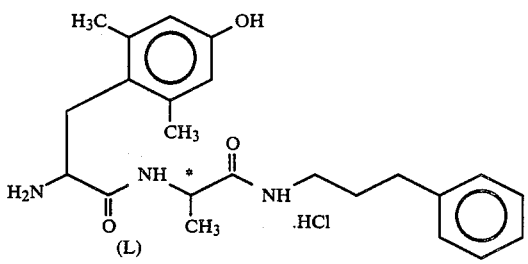

(S—2,6-Me₂Tyr—Ala—PPA.HCl)

The title compound was prepared by the method of Example 4 from diastereomer S of Example 63.

$[\alpha]_D$ —105.0; (MeOH)

Analysis Calcd. for $C_{23}H_{32}N_3O_3Cl \cdot \frac{1}{4}H_2O$ (438.49): C, 63.00; H, 7.47; N, 9.58; Cl, 8.08. Found: C, 63.01; H, 7.40; N, 9.31; Cl, 8.13.

Example 66

N-[(1,1-dimethylethoxy)carbonyl]-2,6-dimethyl-DL-tyrosyl-2-methyl-N-(3-phenylpropyl)alaninamide, (2-methylpropyl)carbonate (ester)

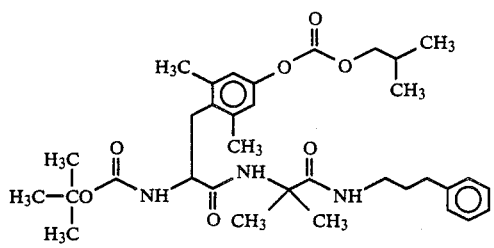

(Boc—(DL)2,6-Me₂Tyr(IBC)—Aib—PPA)

The title compound was isolated from the reaction mixture of a large-scale preparation of the title compound of Example 46 by PLC eluting with 1-3% of EtOH/CH₂Cl₂.

Analysis Calcd. for $C_{34}H_{49}N_3O_7$ (611.80); C, 66.75; H, 8.07; N, 6.87. Found: C, 66.63; H, 7.71; N, 6.89.

Example 67

2,6-dimethyl-DL-tyrosyl-2-methyl-N-(3-phenylpropyl)alaninamide, (2-methylpropyl)carbonate (ester), monohydrochloride

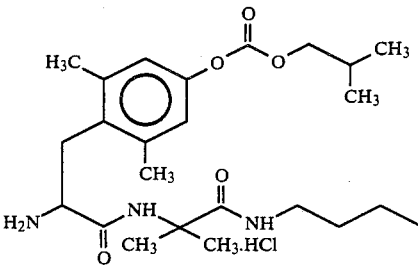

((DL)2,6-Me₂Tyr(IBC)—Aib—PPA.HCl)

The title compound was prepared by the method of Example 4 from the product of Example 66.

Analysis Calcd. for $C_{29}H_{42}N_3O_5Cl$ (MW=548.14): C, 63.55; H, 7.85; N, 7.67; Cl, 6.47. Found: C, 63.43; H, 7.62; N, 7.62; Cl, 6.37.

Example 68 phenylmethyl[1-[[(3-phenylpropyl)amino]carbonyl]pentyl]carbamate

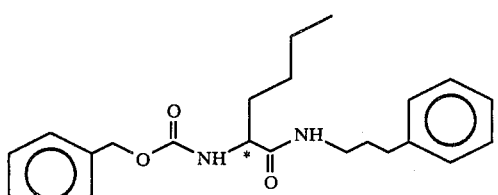

(Z—(D)Nle—PPA)

The title compound was prepared by the method of Example 1 using carbobenzoxy-(D)norleucine (Z-(D)Nle) and used without chromatographic separation.

Example 69

2R-amino-N-(3-phenylpropyl)hexanamide

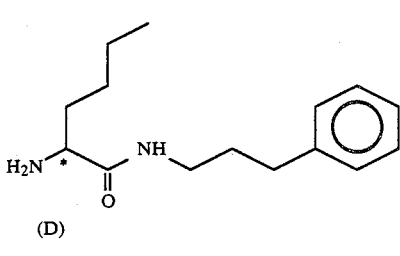

((D)Nle—PPA)

The title compound was prepared by the method of Example 2 from the title material of Example 68 and used in the succeeding Example without purification.

Example 70

N-[(1,1-dimethylethoxy)carbonyl]-2,6-dimethyl-DL-tyrosyl-N-(3-phenylpropyl)-D-norleucinamide

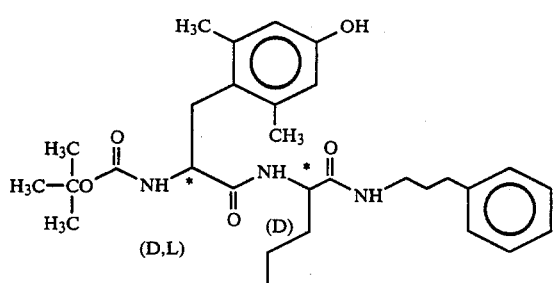

(Boc—(DL)2,6-Me₂Tyr—(D)Nle—PPA)

The title mixture of two diastereomer compounds was prepared and separated as described in Example 3.

Diastereomer F [α]$_D$−1.5; (MeOH)

Analysis Calcd. for C₃₁H₄₅N₃O₅ (MW=539.71); C, 68.99; H, 8.40; N, 7.79. Found: C, 68.96; H, 8.41; N, 7.70.

Diastereomer S [α]$_D$+69.4 (MeOH)

Analysis Calcd. for C₃₁H₄₅N₃O₅ (MW-539.71) C, 68.99; H, 8.40; N, 7.79. Found: C, 69.01; H, 8.46; N, 7.74.

Example 71

2,6-dimethyltyrosyl-N-(3-phenylpropyl)-D-norleucinamide, monohydrochloride (fast isomer)

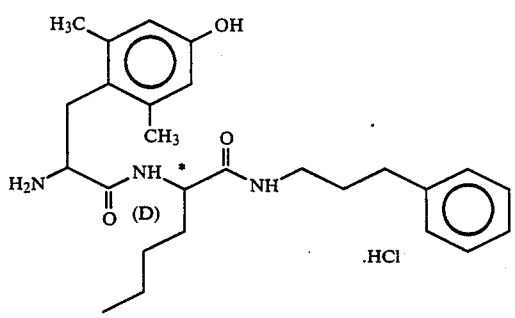

(F—2,6-Me₂Tyr—(D)Nle—PPA.HCl)

The title compound was prepared by method of Example 4 from the F-diastereomer of the title material of Example 70.

[α]$_D$−61.0; (MeOH)

Analysis Calcd. for C₂₆H₃₈N₃O₃Cl.½H₂O (MW=485.07): C, 64.37; H, 8.12; N, 8.67; Cl, 7.31. Found: C, 64.60; H, 8.15; N, 8.65; Cl, 7.88.

Example 72

2,6-dimethyltyrosyl-N-(3-phenylpropyl)-D-norleucinamide, monohydrochloride (slow isomer)

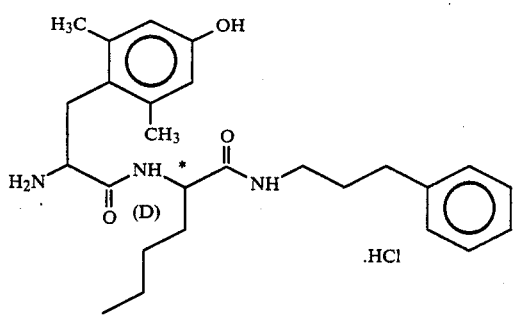

(S—2,6-Me₂Tyr—(D)Nle—PPA.HCl)

The title compound was prepared by the method of Example 4 from the S-diastereomer of the title compound of Example 70.

[α]$_D$+101.8; (MeOH)

Analysis Calcd. for C₂₆H₃₈N₃O₃Cl.½H₂O (MW=485.07): C, 64.37; H, 8.12; N, 8.67; Cl, 7.31. Found: C, 64.57; H, 8.18; N, 8.65; Cl, 7.36.

Example 73 phenylmethyl[1-methyl-1-[[(3-phenylpropyl)amino]carbonyl]propyl]

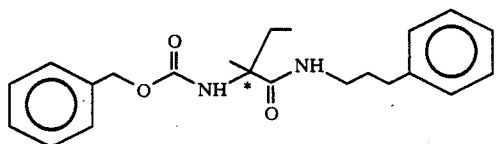

(Z—Iva—PPA)

The title compound was prepared by the method of Example 1 using Z-isovaline (Iva) in place of Z-(D)Ala. The reaction product was used with purification.

Example 74

2-amino-2-methyl-N-(3-phenylpropyl)butanamide

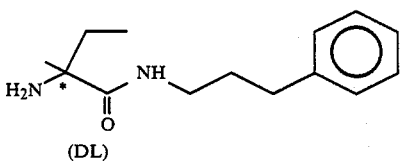

(Iva—PPA)

The title compound was prepared by the method of Example 2 and used in the following Example 75 without purification.

Example 75

N-[(1,1-dimethylethoxy)carbonyl]-2,6-dimethyl-DL-tyrosyl-N-(3-phenylpropyl)-DL-isovalinamide

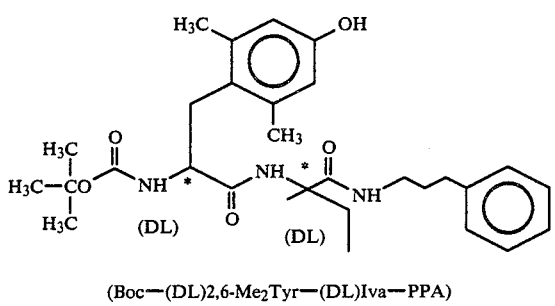

(Boc—(DL)2,6-Me₂Tyr—(DL)Iva—PPA)

The title mixture of two enantiomeric pairs of compounds was prepared and separated as described in Example 3.

Enantiomeric pair A (fast pair)
Analysis Calcd. for $C_{30}H_{43}N_3O_5$ (MW=525.69): C, 68.54; H, 8.24; N, 7.99. Found: C, 67.59; H, 8.69; N, 7.69.

Enantiomeric pair B (slow pair)
Analysis Calcd. for $C_{30}H_{43}N_3O_5$ (MW=525.69): C, 68.54; H, 8.24; N, 7.99. Found: C, 67.73; H, 8.54; N, 7.64.

Example 76

2,6-dimethyltyrosyl-N-(3-phenylpropyl)isovalinamide, monohydrochloride (isomer A)

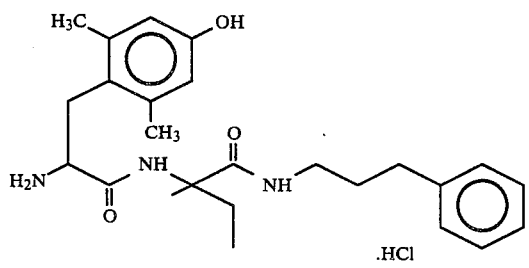

(A—2,6-Me₂Tyr—Iva—PPA.HCl)

The tile compound was prepared by the method of Example 4 from the A-enantiomeric pair of the title compounds of Example 75.

Analysis Calcd. for $C_{25}H_{36}N_3O_3Cl.\frac{1}{2}H_2O$ (MW=471.04): C, 63.74; H, 7.93; N, 8.92; Cl, 7.53. Found: C, 63.31; H, 7.80; N, 8.47; Cl, 7.75.

Example 77

2,6-dimethyltyrosyl-N-(3-phenylpropyl)isovalinamide, monohydrochloride (isomers B)

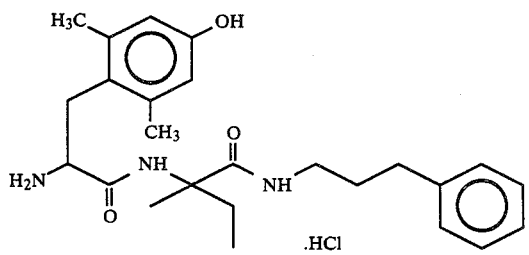

(B-2, 6-Me₂Tyr—Iva—PPA.HCl)

The title compound was prepared by the method of Example 4 from the B-enantiomeric pair of the title compounds of Example 75.

Analysis Calcd. for $C_{25}H_{38}N_3O_3Cl.\frac{1}{2}H_2O$ (MW=471.04): C, 63.74; H, 7.97; N, 8.92; Cl, 7.53. Found: C, 63.42; H, 8.09; N, 8.29; Cl, 7.67.

Example 78

Analgesic properties of the substituted tyrosyl alanine dipeptide amides

The receptor binding and biological properties of the following compounds of this invention are illustrated in Tables 1 and 2 utilizing the previously described opiate binding, hot plate, tail flick, writhing assay, cholera test or hypertensive test. The standard screening dose for the hot plate test of Table 1 was 10 mg/kg i.v. and for the writhing assay was 10 mg/kg s.c. and p.o.

The data presented in Table 2 indicate that a compound of the present invention (Example 5) is distinguishable from the prior art compound. In addition, these data support the assertion that the compound of Example 5 is unexpectedly superior to the vavrek compound as an analgesic. This claim of unexpected superiority is based upon the greater potency of the compound of Example 5 in three different analgesiometric tests and its improved ratio of oral to parenteral activity. The data of Table 2 supporting these claims is briefly summarized below:

The compound of Example 5 binds with tenfold greater affinity to the opiate receptor than does the prior art compound. This enhanced affinity for the opiate receptor was also apparent in studies of the relative affinity of these compounds for the mu and delta receptor subtypes. The compound of Example 5 was more potent as an analgesic than was the prior art as measured by three different analgesiometric tests. Although approximately equipotent in the writhing test following subcutaneous administration, the compound of Example 5 was 6 times more active than the prior art in this test when administered orally. The compound of prior art was not active in the combined tail flick/hot plate analgesiometric tests following administration of doses as great as 100 mg/kg p.o. and 50 mg/kg s.c. In contrast, the compound of Example 5 was active in both tests following oral and subcutaneous administration. In the three analgesiometric tests, the compound of Example 5 was active when administered orally.

TABLE 1

| | Analgesic Properties | | |
| --- | --- | --- | --- |
| | Opiate | Writhing Mouse[b,c] | |
| Compound of | Binding[a] | Subc. | Oral |
| Example 4 | $5.0 \times 10^{-8}$ | 0.58 | 2.39 |
| Example 5 | $2.7 \times 10^{-8}$ | 0.52 | 0.53 |
| Prior Art[d] | $4.3 \times 10^{-7}$ | 3.10 | 0.58 |
| Example 38 | $1.6 \times 10^{-7}$ | Active | Active |
| Example 39 | $5.0 \times 10^{-10}$ | Active | Active |
| Example 27 | $2.7 \times 10^{-9}$ | Active | Active |
| Example 43 | $1.3 \times 10^{-7}$ | Active | Active |

[a]IC₅₀ expressed as moles/liter
[b]ED₅₀ expressed as mg/kg
[c]Active refers to the effect of the screening dose (10 mg/kg).
[d]Prior Art compound is that of Example 5 without the 2 and 6 methyls on the tyrosine.

TABLE 2

| Testing Procedure | Comparative Results | |
|---|---|---|
| | Compound of Prior Art | Compound of Example 5 |
| Opiate Receptor Binding: ($IC_{50}$) | $4.3 \times 10^{-7}$ M | $2.7 \times 10^{-8}$ M |
| Mu Receptor: ($IC_{50}$) | $8.8 \times 10^{-9}$ M | $1.0 \times 10^{-10}$ M |
| Delta Receptor: ($IC_{50}$) | $6.2 \times 10^{-8}$ M | $1.2 \times 10^{-9}$ M |
| Writhing: ($ED_{50}$) | 0.6 mg/kg p.o. | 0.5 mg/kg p.o. |
| | 3.1 mg/kg s.c. | 0.5 mg/kg s.c. |
| Hot Plate (I.V.) | | |
| 10 mg/kg: | Inactive 0/10 | Active 6/7 |
| Rat Cholera Test: ($ED_{50}$) | Inactive at 20 mg/kg s.c. | 6.1 mg/kg s.c. |
| SHR Blood Pressure: | Active at 10 mg/kg i.v. | 1 mg/kg i.v. |
| Combined Tail Flick/Hot Plate | | |
| Tail Flick: ($ED_{50}$) | Inactive at 100 mg/kg p.o. 50 mg/kg s.c. | 115 mg/kg p.o. 35 mg/kg s.c. |
| Hot Plate: ($ED_{50}$) | Inactive at 100 mg/kg p.o. 50 mg/kg s.c. | 52 mg/kg p.o. 9 mg/kg s.c. | p.o. - oral
s.c. - subcutaneous
Prior Art compound is the compound of Example 5 without methyl groups on tyrosine.

Example 53

Antihypertensive properties of the substituted tyrosyl alanine dipeptide amides The following compounds of the invention were evaluated for their antihypertensive properties using the spontaneous hypertensive rat (SHR). This rat exhibited a genetically-linked hypertension that is similar to essential hypertension in humans. The SHR test was essentially that described earlier. Each compound listed in Table 3, was administered intravenously to one unanesthetized, male, spontaneously hypertensive rat; the dosage was 10 mg/kg. Any compound that resulted in a decrease in arterial blood pressure of 20 mm Hg or greater was considered active.

TABLE 3

| Antihypertensive Properties | |
|---|---|
| Compound of | Result |
| Example 4 | Active |
| Example 5 | Active |
| Prior Art | Active |
| Example 16 | Active |
| Example 17 | Active |
| Example 24 | Active |

ROUTE A

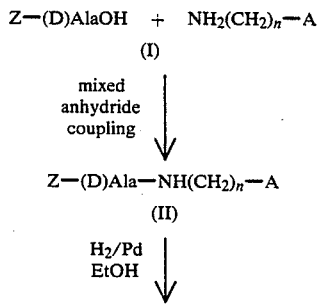

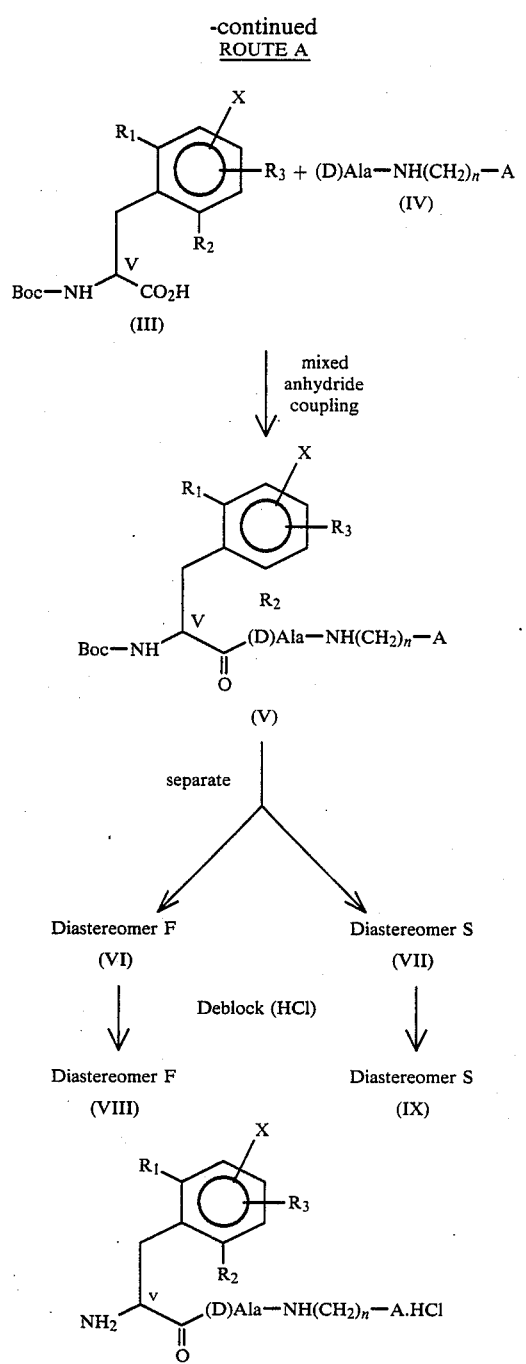

flow sheet 1

ROUTE B

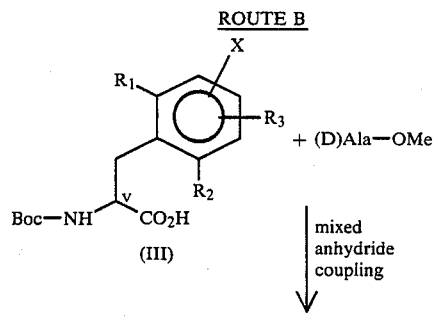

-continued
ROUTE B

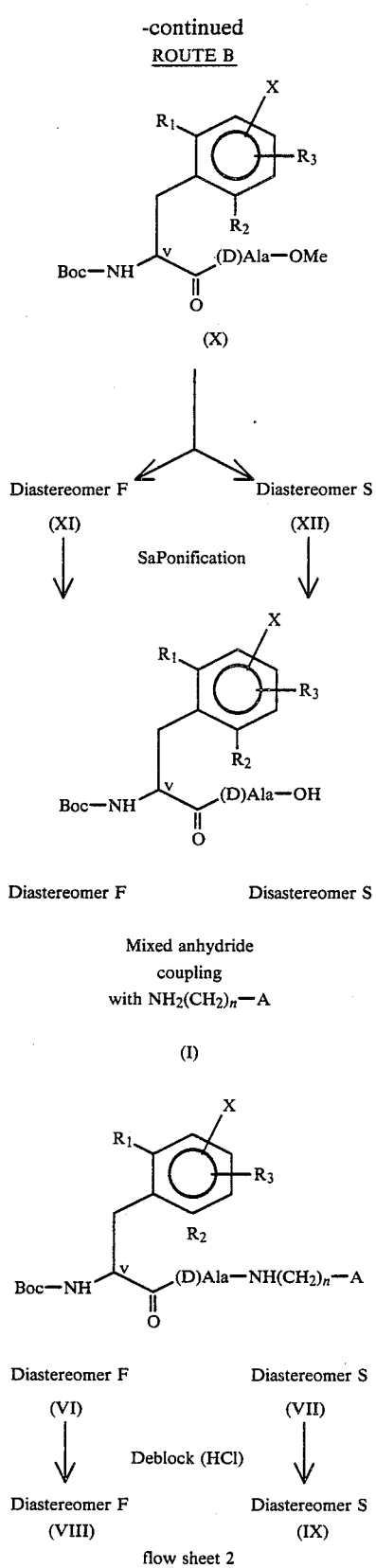

Diastereomer F (XI)  Diastereomer S (XII)

SaPonification

Diastereomer F  Diastereomer S

Mixed anhydride coupling with NH$_2$(CH$_2$)$_n$—A (I)

Diastereomer F (VI)  Diastereomer S (VII)

Deblock (HCl)

Diastereomer F (VIII)  Diastereomer S (IX)

flow sheet 2

We claim:

1. A compound of the formula:

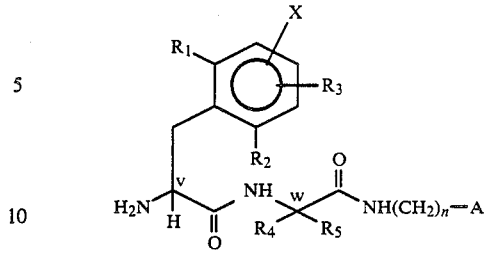

and the pharmaceutically acceptable acid addition salts thereof wherein

R$_1$ represents straight or branched lower alkyl having 1 to 4 carbons;

R$_2$ represents hydrogen, hydroxy, —OCO$_2$R$_1$ substituent or lower alkyl having 1 to 4 carbons;

R$_3$ represents a hydrogen or lower alkyl having 1 to 6 carbons;

R$_4$ and R$_5$ may be the same or different and represent hydrogen or lower alkyl having 1 to 6 carbons;

n is an integer from 1 to 2 or 4 to 6;

X represents a hydrogen, hydroxy or OCO$_2$R$_1$ substituent;

A represents a cyclohexyl, phenyl or phenyl substituted with one or more lower alkyls containing 1 to 6 carbons, one or more amino, hydroxy, halogen, nitro or lower alkoxy substituent having 1 to 6 carbons;

V represents the asymmetric carbon that may be racemic or have the D or L configuration;

W represents the asymmetric carbon when R$_4$ and R$_5$ are not the same that may be racemic or have the D or L configuration.

2. A compound according to claim 1, having the formula

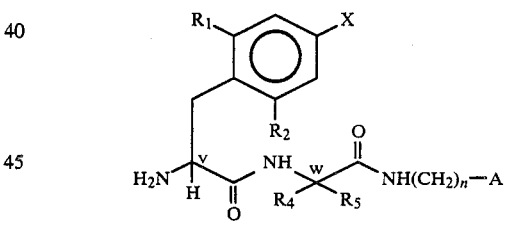

and the pharmaceutically acceptable acid addition salts thereof wherein R$_1$ and R$_2$ are lower alkyl having 1 to 4 carbons, R$_4$ and R$_5$ may be the same or different and represent hydrogen, or lower alkyl having 1 to 6 carbons; X represents a hydrogen, hydroxy or —OCO$_2$R$_1$ substituent; n is an integer from 1 to 2 or 4 to 6; A represents cyclohexyl, phenyl or phenyl substituted with one or more of lower alkyls having 1 to 6 carbons or lower alkoxy having 1 to 6 carbons, one or more amino, hydroxy, halogen or nitro substituents; V represents the asymmetric carbon that may be racemic or have optionally the D or L configuration; W represents the asymmetric carbon when R$_4$ and R$_5$ are not the same that may be racemic or have the D or L configuration.

3. A compound according to claim 2 wherein A is cyclohexyl.

4. A compound according to claim 2 wherein A is phenyl.

* * * * *

UNITED STATES PATENT AND TRADEMARK OFFICE
CERTIFICATE OF CORRECTION

PATENT NO. : 4,727,189
DATED : February 23, 1988
INVENTOR(S) : Hansen, Jr., et al.

It is certified that error appears in the above-identified patent and that said Letters Patent is hereby corrected as shown below:

Column 19, the second structure, that portion of the structure, reading

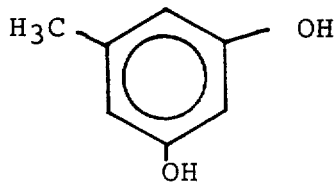   should read   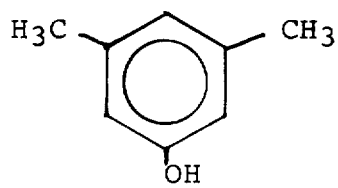

Column 40, line 38, reading "delta receptor" should read -- delta opiate receptor --.

Signed and Sealed this

Twentieth Day of June, 1989

Attest:

DONALD J. QUIGG

Attesting Officer

Commissioner of Patents and Trademarks